US005344395A

United States Patent [19]

Whalen et al.

[11] Patent Number: 5,344,395

[45] Date of Patent: Sep. 6, 1994

[54] APPARATUS FOR INTRAVASCULAR CAVITATION OR DELIVERY OF LOW FREQUENCY MECHANICAL ENERGY

[75] Inventors: Mark J. Whalen, Alexandria; Lloyd K. Willard, Miltona, both of Minn.

[73] Assignee: SciMed Life Systems, Inc., Maple Grove, Minn.

[21] Appl. No.: 826,959

[22] Filed: Jan. 24, 1992

Related U.S. Application Data

[63] Continuation-in-part of Ser. No. 435,280, Nov. 13, 1989, Pat. No. 5,085,662.

[51] Int. Cl.$^5$ .............................................. A61B 17/22

[52] U.S. Cl. ...................................... 604/22; 606/159; 606/169

[58] Field of Search ....................... 606/169, 171, 159; 604/22; 128/24 AA

[56] References Cited

U.S. PATENT DOCUMENTS

| | | |
|---|---|---|
| 2,874,470 | 2/1959 | Richards . |
| 3,089,790 | 5/1963 | Balamuth . |
| 3,352,303 | 11/1967 | Delaney . |
| 3,433,226 | 3/1969 | Boyd . |
| 3,565,062 | 2/1971 | Kuris . |
| 3,570,476 | 3/1971 | Gregg . |
| 3,584,327 | 4/1971 | Murry . |
| 3,589,363 | 6/1971 | Banko . |
| 3,614,953 | 10/1971 | Moss . |
| 3,659,607 | 5/1972 | Banko . |
| 3,730,185 | 5/1973 | Cook . |
| 3,776,238 | 12/1973 | Peyman et al. ..................... 606/171 |
| 3,805,787 | 4/1974 | Banko . |
| 3,811,446 | 5/1974 | Lerwick . |
| 3,823,717 | 7/1974 | Pohlman . |
| 3,830,240 | 8/1974 | Antonevich . |
| 3,861,391 | 1/1975 | Antonevich . |
| 3,874,372 | 4/1975 | Le Bon . |
| 3,896,811 | 7/1975 | Storz . |
| 3,941,122 | 3/1976 | Jones . |
| 3,990,452 | 11/1976 | Murry . |
| 4,030,505 | 6/1977 | Tessler . |
| 4,063,557 | 12/1977 | Wuchinich . |
| 4,188,952 | 2/1980 | Loschilov . |
| 4,192,294 | 3/1980 | Vasilevsky . |
| 4,216,766 | 8/1980 | Duykers . |
| 4,223,676 | 9/1980 | Wuchinich . |
| 4,248,232 | 2/1981 | Engelbrecht . |
| 4,315,511 | 2/1982 | Chin . |
| 4,330,278 | 5/1982 | Martin . |
| 4,343,301 | 8/1982 | Indech . |
| 4,406,284 | 9/1983 | Banko . |
| 4,417,578 | 11/1983 | Banko . |
| 4,425,115 | 1/1984 | Wuninich . |
| 4,428,748 | 1/1984 | Peyman . |
| 4,431,006 | 2/1984 | Trimmer et al. .......... 128/24 AA X |

(List continued on next page.)

FOREIGN PATENT DOCUMENTS

| | | |
|---|---|---|
| 232678B1 | 4/1991 | European Pat. Off. . |
| WO8905611 | 6/1989 | World Int. Prop. O. . |

*Primary Examiner*—Michael H. Thaler
*Attorney, Agent, or Firm*—Nawrocki, Rooney & Sivertson

[57] ABSTRACT

An apparatus and method for recanalization of a blood vessel obstruction by application of low frequency mechanical energy to a vessel site or by creation of cavitation at the vessel site. The system includes a catheter assembly having a wire located within and extending through a wire support tube and adapted to move axially therewith. A driving apparatus positioned at a proximal portion of the catheter assembly imparts energy to the wire to oscillate it axially. A tip is connected to a distal end of the wire and imparts low frequency mechanical energy or causes cavitation at the vessel site to recanalize it. Further, a fluid particle removal system can be incorporated within the catheter assembly to convey pressurized fluid via the wire support tube to the tip where the fluid is redirected in a proximal direction into a second tube of the catheter assembly coaxially positioned around the wire support tube. Particulate from the vessel obstruction being recanalized becomes attached viscously in the redirected pressurized fluid and is withdrawn from the vessel site.

1 Claim, 25 Drawing Sheets

U.S. PATENT DOCUMENTS 4,445,509 5/1984 Auth .
4,474,180 10/1984 Angulo ...................... 128/24 AA X
4,493,694 1/1985 Wachinich .
4,504,264 3/1985 Kelman .
4,515,583 5/1985 Sorich .
4,516,398 5/1985 Wuchinich .
4,526,571 7/1985 Wuchinich .
4,576,177 3/1986 Webster .
4,582,181 4/1986 Samson .
4,587,972 5/1986 Morantte .
4,609,368 9/1986 Dotson .
4,617,931 10/1986 Dory .
4,631,052 12/1986 Kensey .
4,634,419 1/1987 Kreizman .
4,634,420 1/1987 Spinosa .
4,643,186 2/1987 Rosen .
4,643,717 2/1987 Cook .
4,669,469 6/1987 Gifford .
4,679,557 7/1987 Opie .
4,681,561 7/1987 Hood .
4,685,458 8/1987 Leckrone .
4,692,139 9/1987 Stiles .
4,696,668 9/1987 Wilcox .
4,698,058 10/1987 Greenfeld .
4,722,340 2/1988 Takayama .
4,729,373 3/1988 Peyman .
4,735,604 4/1988 Watmough .
4,741,713 5/1988 Starck .
4,747,820 5/1988 Hornlein .
4,747,821 8/1989 Kensey .
4,748,971 6/1988 Borodulin .
4,749,376 6/1988 Kensey .
4,750,488 6/1988 Wuchinich .
4,750,902 6/1988 Wuchinich .
4,762,129 8/1988 Bonzel .
4,765,332 8/1988 Fischell .
4,768,496 9/1988 Kreizman .
4,781,186 11/1988 Simpson .
4,781,677 11/1988 Wilcox .
4,794,931 1/1989 Yock .
4,804,364 2/1989 Dieras .
4,808,153 2/1989 Parisi .
4,816,017 3/1989 Hood .
4,816,018 3/1989 Parisi .
4,819,635 4/1989 Shapiro .
4,823,793 4/1989 Angulo .
4,827,911 5/1989 Broadwin .
4,838,853 6/1989 Parisi .
4,846,192 7/1989 MacDonald .
4,846,790 7/1989 Hornlein .
4,847,047 7/1989 Groetsch .
4,854,325 8/1989 Stevens .
4,861,332 8/1989 Parisi .
4,867,141 9/1989 Nakada .
4,911,170 3/1990 Thomas .
4,917,085 4/1970 Smith .
4,920,954 5/1990 Alliger .
4,930,515 6/1990 Terwilliger .
4,936,281 6/1990 Terwilliger .
4,936,307 6/1990 Saito .
4,936,845 6/1990 Stevens .
4,940,468 7/1990 Petillo ............................... 604/22 X
4,950,277 8/1990 Farr .
5,024,651 6/1991 Shiber .
5,042,984 8/1991 Kensey .
5,085,662 2/1992 Willard .
5,127,917 7/1992 Niederhauser et al. ............ 606/191
5,163,433 11/1992 Kagawa et al. ........... 128/24 AA X

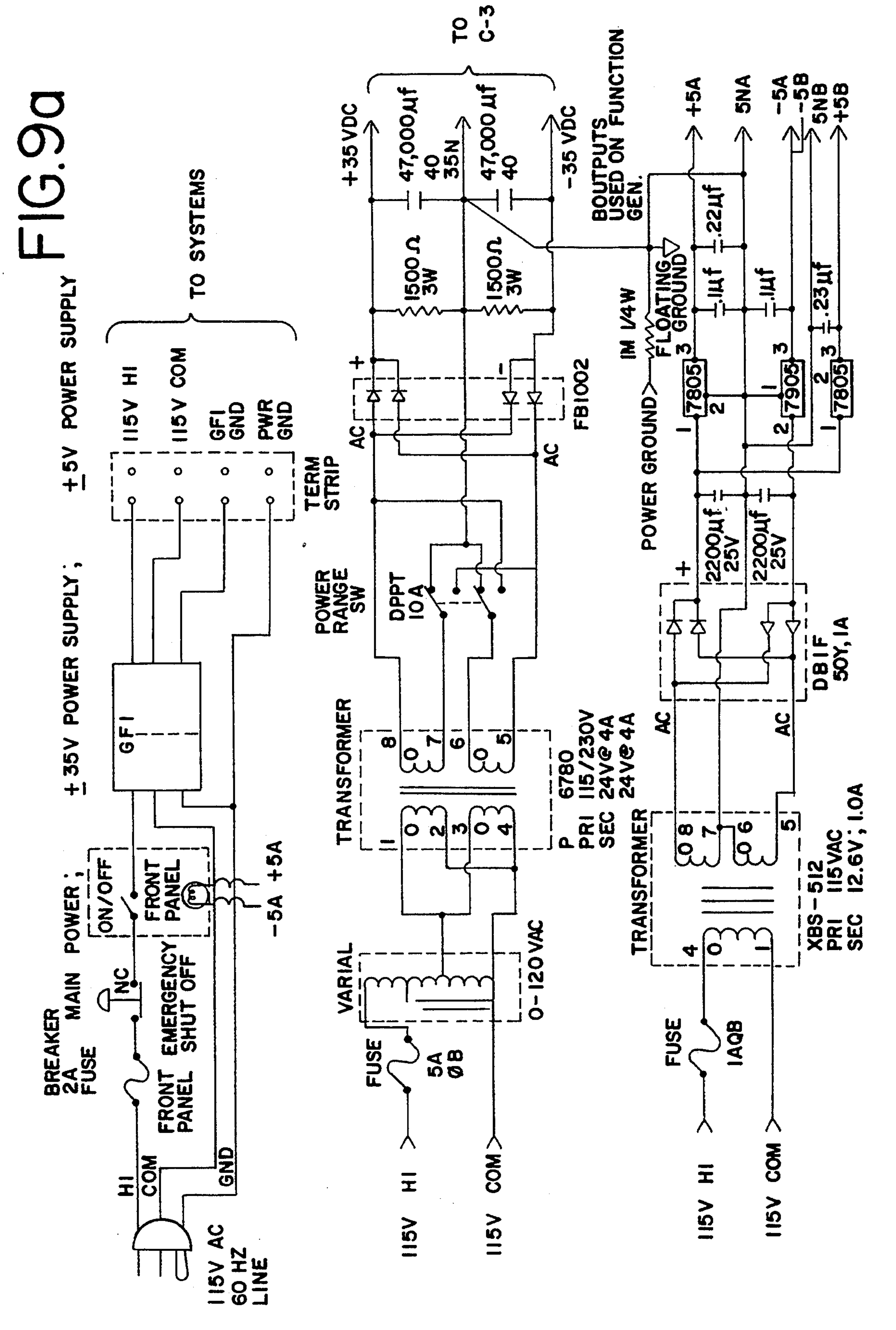
FIG.9a
±35V POWER SUPPLY; ±5V POWER SUPPLY
TO SYSTEMS
115V HI
115V COM
GFI GND
PWR GND
TERM STRIP
GFI
POWER; ON/OFF
FRONT PANEL
BREAKER 2A FUSE
MAIN NC
FRONT PANEL EMERGENCY SHUT OFF
HI
COM
GND
115V AC 60 HZ LINE
-5A +5A
TO C-3
+35 VDC
47,000μf 40
35N
47,000μf 40
-35 VDC
1500Ω 3W
1500Ω 3W
FB1002
AC
POWER RANGE SW
DPPT 10A
TRANSFORMER
6780
P
PRI 115/230V
SEC 24V@4A 24V@4A
VARIAL
0-120VAC
FUSE
5A ØB
115V HI
115V COM
BOUTPUTS USED ON FUNCTION GEN.
+5A
5NA
-5A
-5B
5NB
+5B
.22μf
.1μf
.1μf
.23μf
FLOATING GROUND
IM 1/4W
POWER GROUND
7805
7905
7805
2200μf 25V
2200μf 25V
DB1F 50Y, 1A
XBS-512
PRI 115VAC
SEC 12.6V; 1.0A
FUSE
1AQB
115V HI
115V COM FIG. 11c
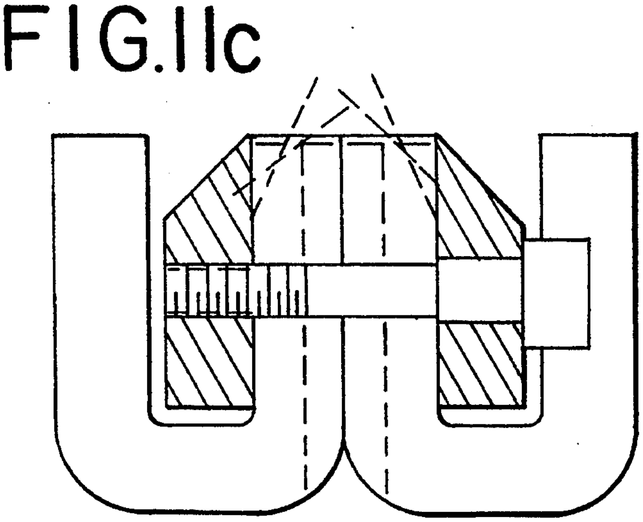
FIG. 11c'
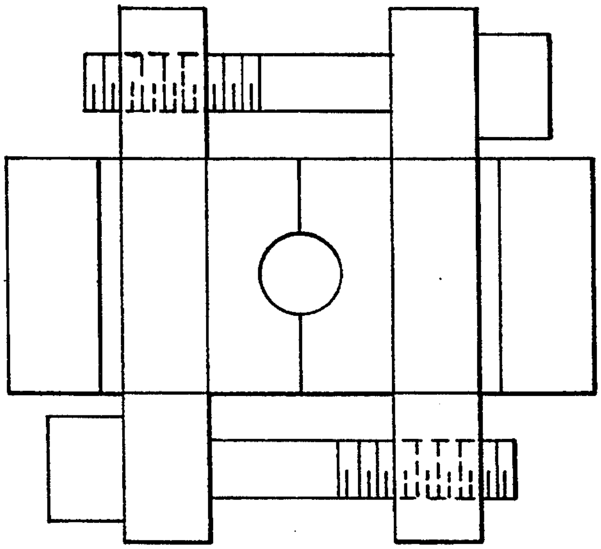
FIG. 11c"
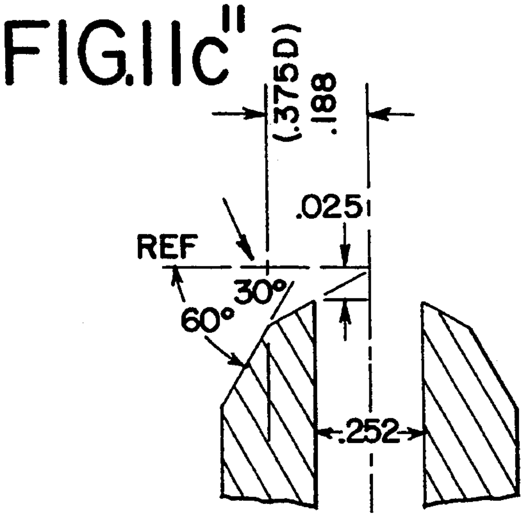

FIG. 11d
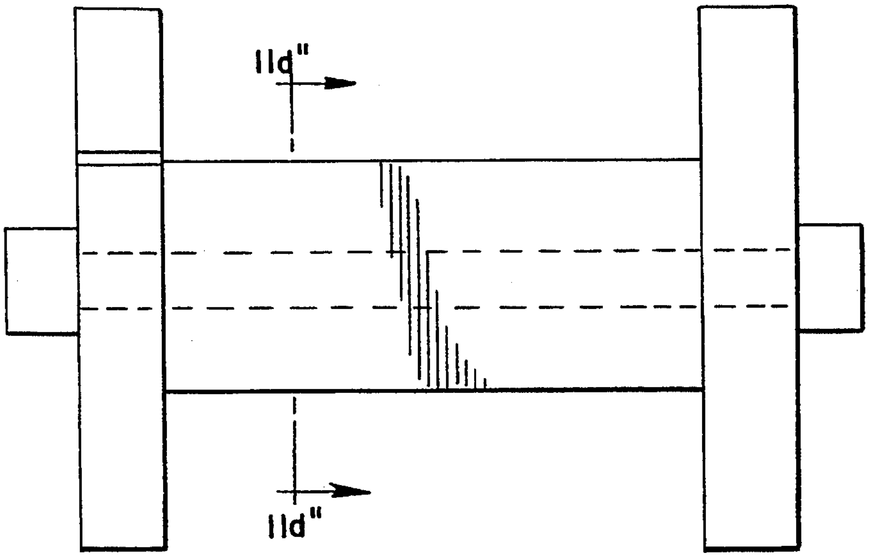
FIG. 11d'
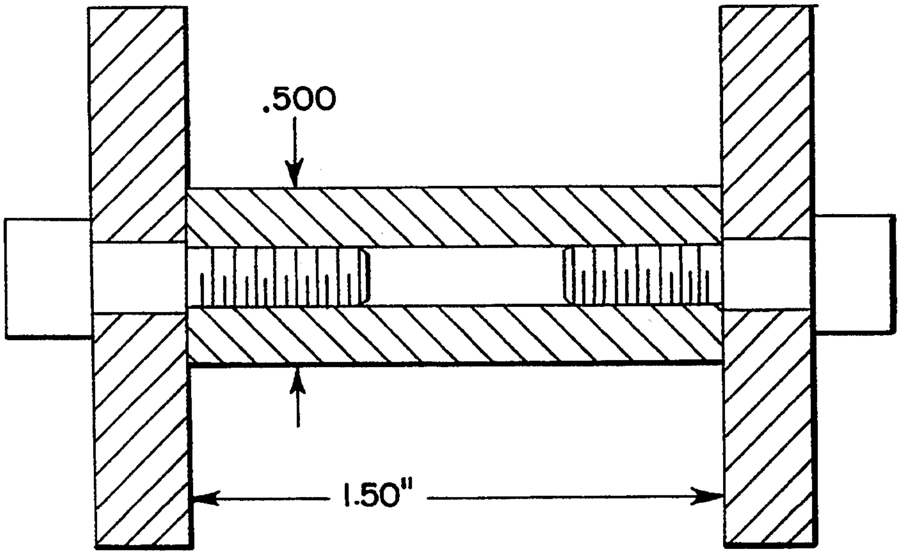
FIG. 11d"
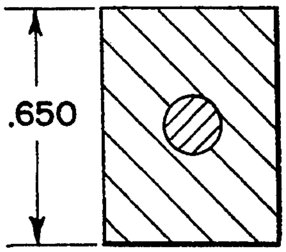

FIG. 12

$W := 2 \cdot X \cdot f_{NATURAL}$ $\quad$ $VEL := y \cdot W$ $\quad$ $VEL = 3.203$ m/s

FLOW ASSUMPTIONS:

PULMONARY ARTERY PRESSURE $P_O := (3200 + 101356)$ Pa

BLOOD VAPOR PRESSURE (SAME AS WATER): $P_V := 4240$ Pa

BLOOD DENSITY (SAME AS WATER): $DENS_{BLOOD} := 995.7$

BLOOD FLOW VELOCITY: $V_{BLOOD} := 1.33$ m/s

BECAUSE OF BLOCKAGE ASSUME VBLOOD = 0 $\quad V_{BLOOD} := 0$

MINIMUM VELOCITY OF TIP TO START CAVITATION (K.CAVE = .75)

$K_{CAV} := .75$ $$V_{MIN.} := \sqrt{2 \cdot \frac{P_O - P_V}{DENS_{BLOOD} \cdot K_{CAV}}} \qquad V_{MIN} = 16.391 \text{ m/s}$$

CALCULATING THE MINIMUM DISPLACEMENT REQUIRED TO OBTAIN CAVITATION AT A GIVEN FREQUENCY. DISPLACEMENT IS AMPLITUDE, PEAK TO PEAK IS DOUBLE THE DISPLACMENT.

$i := 1, 2 \, .. 50$ $\qquad$ $A_i := \frac{V_{MIN.}}{2 \cdot X \cdot f_{OP_i}}$ $f_{OP_i} := 100 \cdot i$

PLOT OF TIP AMPLITUDE VERSUS FREQUENCY FOR A .75 CAVITATION NO.

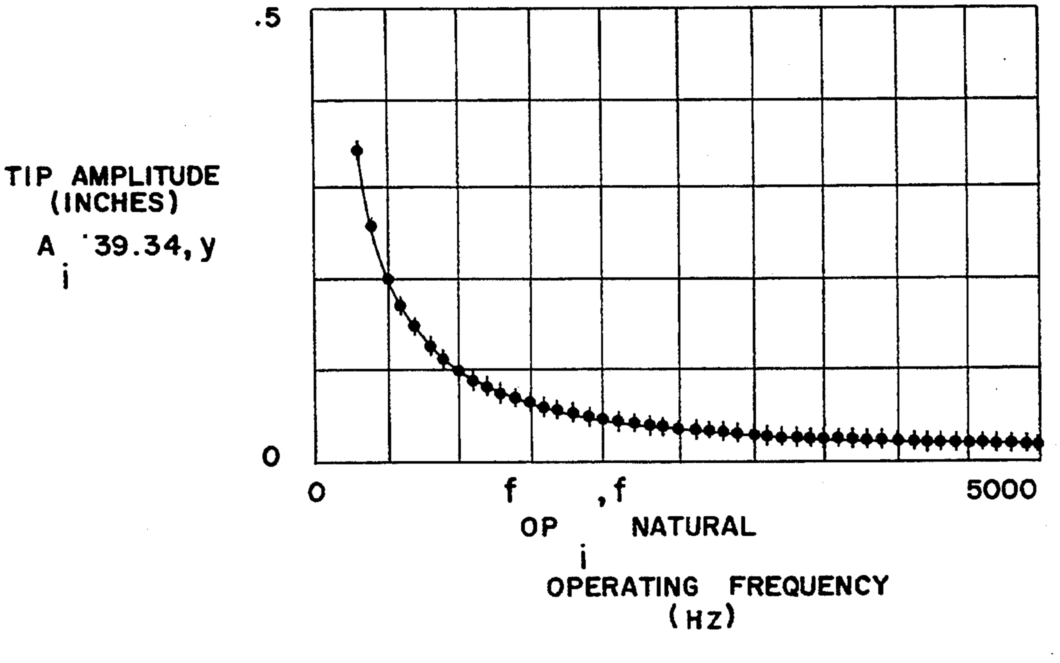

APPARATUS FOR INTRAVASCULAR CAVITATION OR DELIVERY OF LOW FREQUENCY MECHANICAL ENERGY

RELATION TO OTHER APPLICATIONS

The present application is a continuation in part of Ser. No. 07/435,280, filed Nov. 13, 1989 now U.S. Pat, No. 5,085,662 issued Feb. 4, 1992.

BACKGROUND OF THE INVENTION

The present invention relates to a new intravascular apparatus and method that can be used as a therapy for diseases of the vascular system that are characterized by an undesired obstruction or restriction of a vascular segment, or that can be used in conjunction with other intravascular therapeutic or diagnostic apparatuses or methods. More particularly, the present invention relates to a new intravascular apparatus and method for recanalization of an obstructed vessel or for removal and/or reduction of undesired material that obstructs or occludes a vessel by application of low frequency mechanical energy to a vessel site or by creation of cavitation at the vessel site.

Obstructive arterial disease continues to be serious health problem in our society today. Obstructive arterial disease can occur in coronary or peripheral arteries. This disease is the result of the deposit and accretion of fatty substances on the interior surface of the walls of the arteries. The build up of such deposits results in a narrowing of the diameter of the artery which restricts the blood flow through the artery. This condition wherein the artery is narrowed is known generally as stenosis.

Various therapies have been considered and developed for the treatment of obstructive vascular disease. One treatment is coronary artery bypass graft surgery. Bypass surgery, however, has the disadvantage that it is extremely invasive and traumatic to the patient. Accordingly, less invasive and less traumatic alternative therapies to bypass surgery are desired.

Several less invasive alternatives to bypass surgery have been developed that rely upon intravascular catheterization. Intravascular catheterization therapies involve the positioning of an elongate tubular catheter incorporating a therapeutic implement via a blood vessel to the site of the vascular obstruction to treat it. One such intravascular procedure is angioplasty. Angioplasty is a procedure in which an inflatable balloon is positioned on the inside of the artery at the site of the lesion and expanded in order to compress the materials at the lesion and thus open the restricted area in the artery. In this procedure, a balloon is attached to the distal end of a small diameter flexible catheter which includes a means for inflating the balloon from the proximal end of the catheter. The catheter is maneuvered through the patient's vessels to the site of the lesion with the balloon in uninflated form. When the uninflated balloon is properly positioned at the lesion, the balloon is then inflated to dilate the restricted area.

Although angioplasty is presently the most well developed and widely used intravascular therapeutic procedure, other intravascular catheterization therapies, such as atherectomy and laser irradiation, have also been considered and developed to a stage of at least limited success. Other therapeutic approaches in addition to these have also been considered and/or developed. Although existing therapies have proven to provide generally good results in many cases of obstructive vascular disease, no one therapy has yet proven to be successful for all cases of vascular disease. Moreover, with existing therapies for obstructive vascular disease, restenosis is observed in a significant percentage of cases following the intravascular procedure. Accordingly, there still is a need for a new therapy for treatment of obstructive vascular diseases.

One therapeutic approach that has been considered for treatment of obstructive vascular disease is the application of ultrasonic mechanical energy to the vascular obstruction. Ultrasound apparatuses and methods have been utilized for the removal or break up of undesired material in body locations other than blood vessels. For example, ultrasonic therapies have been utilized to remove kidney or gall stones and have been applied as well to other undesired materials, such as malignancies. In those therapeutic methods in which ultrasound has been successfully used to remove unwanted material from the body, the material to be removed has been in a location of the body at which a suitable methodology for delivery of the ultrasonic energy to the material could be utilized. One example of such an apparatus is a cell disrupter. A cell disrupter has a mechanical horn that is vibrated at a high natural frequency (e.g. 10–30 kilohertz) to direct ultrasonic energy to undesired cell groups or chemical groups in the body through a medium such as a biological fluid or chemical solution. The delivery of ultrasonic energy to the undesired cell or chemical group operates to break up the group.

Ultrasonic therapeutic methods have been considered for the break up and/or removal of undesired material or occlusions in blood vessels of the body. The use of ultrasonic energy to break up undesired material in the vascular system is promising because of the apparent selectivity in breakdown of undesired obstructive material compared to surrounding healthy tissue upon delivery of energy. Directed ultrasonic mechanical energy appears to selectively break down undesired material in a vascular region, such as plaque or thrombus, while causing no apparent damage to surrounding healthy vessel segments. However, despite the appeal of ultrasonic energy as a therapy for obstructive vascular diseases, it has so far not been successfully used for obstructive vascular diseases. One of the problems associated with the use of ultrasonic therapeutic techniques in the vascular system has been how to deliver the energy to blood vessel sites, especially vessel sites that are deep within the body.

At the present time, distal vessel sites, such as the coronary arteries in which stenosis commonly occurs, are routinely accessed by small diameter guide wires or catheters from remote locations such as the femoral artery for diagnostic and therapeutic procedures, such as angiographies, balloon angioplasties, and atherectomies. Further, physicians and clinicians who practice in this specialty have developed familiarity and skills as well as numerous accessories to assist in cardiovascular catheter and guide wire placement. Accordingly, it would be advantageous to utilize catheters and/or wires for ultrasonic energy delivery to a distal vessel location. However, using catheters and/or guide wires for the delivery of ultrasonic energy has several technical difficulties which have so far presented significant obstacles to the development of this therapy. Guide wires for use in positioning in the coronary tract may have a diameter on the order of 0.010 to 0.018 inches and a length of at least approximately 175 cm. Catheters and guide wires are designed to be flexible longitudinally in order to traverse tortuous vessel paths. Thus, because catheters and wires are usually designed to be flexible, they are not well suited to convey mechanical energy. Accordingly, the very properties desired and necessary in guide wires or catheters in order to position them are the same properties that have made them unsuitable for transmitting ultrasonic energy.

One previously considered approach to conveying ultrasonic energy via a wire to a distal vessel location is to set up a harmonic wave in the wire. According to this approach, a solid wire, made of titanium for example, can be vibrated at its natural frequency (which is a function of its length). A significant problem associated with conveying ultrasonic energy by such a method is that it causes the entire wire to vibrate transversely as well. This transverse motion generates considerable friction which results in undesirable attenuation along the length of the wire thereby resulting in a substantial amount of heat in the vessel. This is an undesirable result that precludes operation for a sufficient period of time to be effective. Moreover, the harmonic wave set up in the wire attenuates quickly if the wire is maintained in a curved configuration which is typical for access to remote vessel locations. These drawbacks have prevented this approach from achieving practical application.

Another concern associated with using ultrasonic techniques in a patient's blood vessel relates to the break up of the undesired material. The break up of undesired materials in a person's body in other body locations, such as in the kidney or gall bladder, by ultrasonic techniques may not be of concern because the presence of smaller, broken-up particles of the undesired material in such locations present little or no serious problem. However in arterial sites, the break up of material may pose problems. Assuming that ultrasonic energy could be successfully applied to a blood vessel obstruction, it is a concern that particles of the broken up occlusion may be carried away to another blood vessel location and cause a restriction of blood flow there. Worse yet, particles of a broken up occlusion may become lodged in other locations causing clots. Prior methods for applying ultrasonic techniques to blood vessels have not addressed capture or removal of particulate from the blood vessel following treatment.

Therefore, it is an object of the present invention to provide an apparatus, system and method for recanalization of an occluded or partially occluded body vessel through the use of delivering mechanical energy to a vessel location.

It is another object of the present invention to provide an apparatus, system, and method for use with other therapeutic methods and apparatuses and which is adapted to provide for recanalization of an occluded or partially occluded vessel at least to a degree to facilitate use of the other therapeutic methods or apparatuses.

It is yet further object of the present invention to provide an apparatus, system, and method for delivering mechanical energy over an elongate wire to a vascular site.

It is still a further object of the present invention to provide an apparatus, system, and method for delivering mechanical energy over an elongate wire to a vascular site without the build up or generation of heat due to transverse wire motion.

It is yet still a further object of the present invention to provide an apparatus, system, and method for removal of undesired material from a arterial site in conjunction with the recanalization of the artery by the delivery of mechanical energy to the artery site.

SUMMARY OF THE INVENTION

According to a first aspect of the invention, there is provided an apparatus and method for recanalization of a blood vessel obstruction by application of low frequency mechanical energy to a vessel site or by creation of cavitation at the vessel site. The system includes a catheter assembly having a wire located within and extending through a wire support tube and adapted to move axially and/or longitudinally therewith. A driving apparatus positioned at a proximal portion of the catheter assembly imparts energy to the wire to oscillate it axially. A tip is connected to a distal end of the wire and imparts low frequency mechanical energy or causes cavitation at the vessel site to recanalize it. The catheter assembly also includes a second tube located around the wire support tube to damp transverse movement of the catheter assembly during oscillation of the tip.

According to a further aspect of the invention, a fluid particle transmission system is incorporated within the catheter assembly to convey pressurized fluid via the wire support tube to the tip where the fluid is redirected in a proximal direction into the second tube of the catheter assembly. Particulate from the vessel obstruction being recanalized becomes attached viscously in the redirected pressurized fluid and is withdrawn from the vessel site.

BRIEF DESCRIPTION OF THE FIGURES

FIGS. 9*a* to 9*h* are circuit diagrams for the power control system of FIG. 8.

FIGS. 11*a* to 11*d* illustrate the steps associated with the construction of the pole shown in FIG. 10.

FIG. 12 is a graph illustrating the relationship between amplitude and frequency that establishes the operating threshold necessary to cause cavitation at the tip during intravascular operation.

DETAILED DESCRIPTION OF THE PRESENTLY PREFERRED EMBODIMENTS

In the detailed description that follows, a first preferred embodiment will be described that utilizes intravascular energy delivery in conjunction with a fluid particle removal system. Next, another preferred embodiment will be described that utilizes intravascular mechanical energy delivery without a fluid particle removal system. Then, further alternative embodiments of the system(s) and/or system components will be described.

I. THE SYSTEM WITH FLUID PARTICLE REMOVAL

A. THE SYSTEM IN GENERAL

Figure 1:
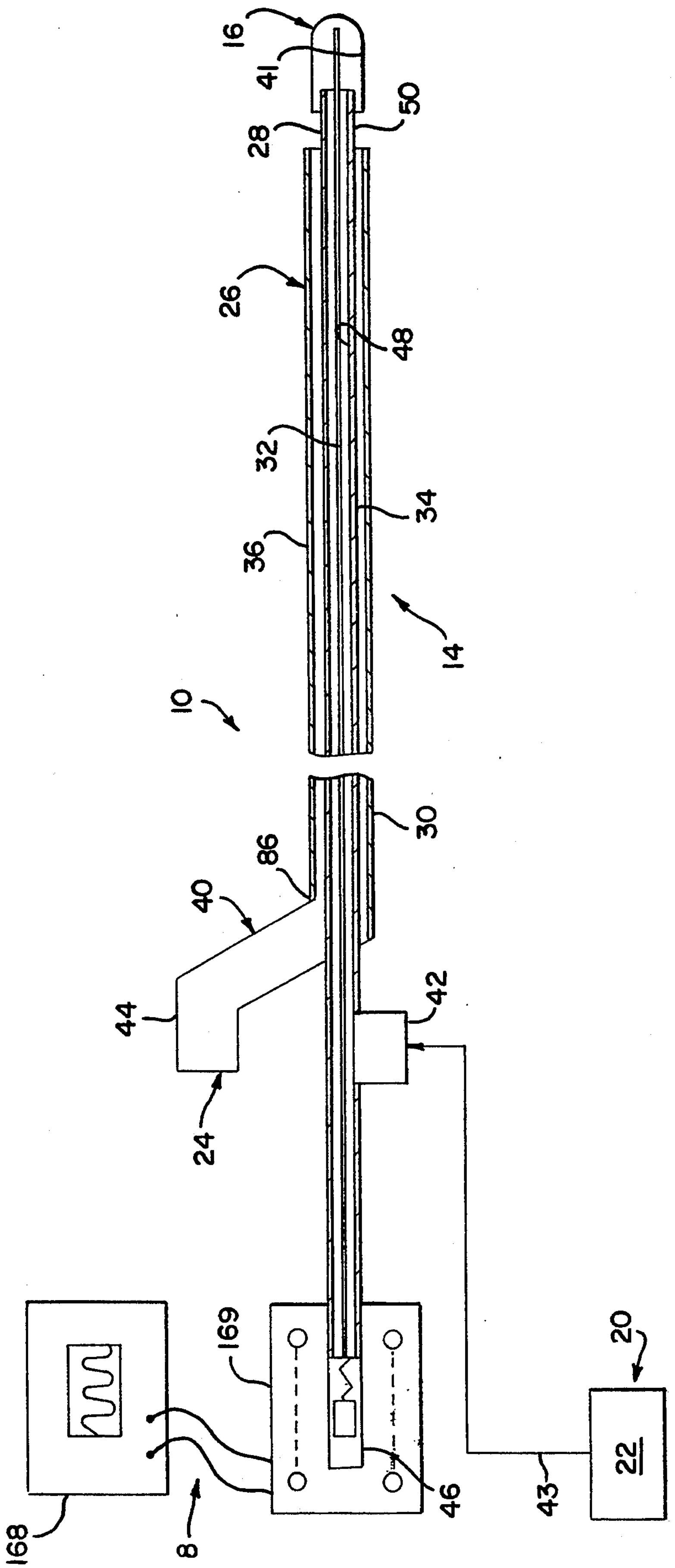
FIG. 1 is a schematic representation of a system that incorporates aspects of a first embodiment of the present invention.

Referring to FIG. 1, there is illustrated a schematic representation of a system 10 according to a first embodiment of the present invention. The system 10 provides for the intravascular delivery of mechanical energy as a therapy by itself or in conjunction with other intravascular therapeutic or diagnostic methods and systems. The quantity of energy delivered with this embodiment is preferably selectable by the user within a range extending from a quantity of energy sufficient to cause cavitation at a vessel site down to a quantity of energy less than the amount required to produce cavitation (e.g. a lower frequency and/or amplitude). The system 10 includes a catheter assembly 14 with an energy delivery tip 16 and a driving apparatus 18. In this embodiment, the system 10 also includes a fluid particle removal system 20 including a pressurized fluid source 22 and a fluid discharge outlet 24.

In a present embodiment, the catheter assembly 14 has a working length of approximately 53.15 inches (135 cm) measured from the distal portion of a proximally-provided manifold to the distal tip 16. In a preferred embodiment for use in the peripheral vasculature, the catheter assembly 14 will have a distal external profile in a range between 0.060 and 0.018 inches. In a preferred embodiment for use in the coronary vasculature, the catheter assembly 14 will have a distal external profile in a range between 0.04 and 0.010 inches. The following preferred embodiment will be described in terms of a catheter assembly 14 suitable for use in the peripheral vasculature. A catheter assembly for use in the coronary vasculature may be provided making corresponding adjustments to the dimensions provided in accordance with the ranges noted above.

B. THE CATHETER ASSEMBLY

1. In General

The catheter assembly 14 has a distal portion 26 sized and adapted to be positioned intravascularly to a site in a patient's blood vessel at which treatment by application of low frequency mechanical energy or by creation of cavitation is to take place. The energy delivery tip 16 is located at a distal end 28 of the catheter assembly distal portion 26. The vessel treatment site may be a location at which an obstruction by undesired material has been determined to be present. The presence and location of the undesired material may be diagnosed by angiographic methods (e.g. dyes) well known in the art. The undesired material may include plaque, stenosis, organized fibrotic, collagen, or atherosclerotic materials.

A proximal portion 30 of the catheter assembly 14 is adapted to be positioned outside of the body of the patient. The driving apparatus 18 is associated with the proximal portion 30 of the catheter assembly 14 and is adapted to activate the delivery of low frequency mechanical energy from the tip 16 or for creation of cavitation at the tip 16. The catheter assembly 14 is composed of a core wire 32 extending therethrough and connected to the tip 16 for the transmission of the energy from the proximal end of the catheter assembly to the distal end. The catheter assembly 14 is also composed of a first tube 34 (also referred to herein as the wire support tube or the supply tube) and a second tube 36 (also referred to herein as the particle removal sheath or the damping sheath) which are coaxially disposed about the core wire 32. The core wire 32 is adapted to move in oscillation axially within the first tube 34, as described in further detail below. The second tube 36 is adapted to reduce or prevent transverse oscillation of the catheter assembly during oscillation of the core wire axially as well as provide additional functions as described further below.

2. Support tube in general

The support tube 34 is adapted to support the core wire 32, maintain a pressure head through the catheter assembly, and reduce fluid flow losses while possessing a sufficiently low profile and flexibility for intravascular use. In both the presently described embodiment that includes fluid particle removal and in the embodiment described below without fluid particle removal, the support tube 34 functions to provide a supporting path through which the core wire 32 can translate axially with minimal loss due to transverse vibration. Accordingly, the support tube 34 provides for radial support for the axially translating core wire 32 from its proximal end to its distal connection to the tip 16. In the present embodiment with fluid particle removal, the support tube 34 also provides an additional function. In the present embodiment, the support tube 34 also provides an annular passage between the core wire 32 and the inner surface of the support tube 34 through which the pressurized fluid can flow distally to the tip.

The annular clearance of the supply tube 34 around the core wire 32 also determines the amount of flow loss through the system. The overall distal profile of the catheter assembly (including the supply tube) is constrained distally (i.e. corresponding approximately to the distal 35 cm) in order to provide intravascular access. In order to reduce flow losses up to this distal location, the annular clearance between the core wire and the supply tube is increased to its maximum allowable size to minimize flow losses through the proximal section of the catheter assembly while maintaining an overall low profile and support for the core wire. The maximum proximal profile of the catheter assembly allows for an annular clearance outside of the catheter assembly for flushing of contrast fluid during a typical procedure when installed in a 7 or 8 French guide catheter.

3. Support tube proximal portion

In the first embodiment, associated with the proximal portion 30 of the catheter assembly 14 is a manifold assembly 40. The manifold assembly 40 includes a first port 42 and a second port 44. The fluid source 22 is adapted to provide fluid 41 (e.g. saline) under pressure to the first port 42 of the manifold assembly 40 via a supply line 43. The first tube 34 is connected in a proximal portion thereof to the first port 42. The first tube 34 extends distally from the first port 42 to the distal portion 26 of the catheter assembly 14 and proximally from the first port 42 to a proximal end 46 of the first tube 34. Hydraulic pressure is transmitted through the catheter assembly 14 via a first tube lumen 48 of the first tube 34 from the fluid source 22 to a distal end 50 of the first tube 34 and then to the tip 16.

Figure 2:
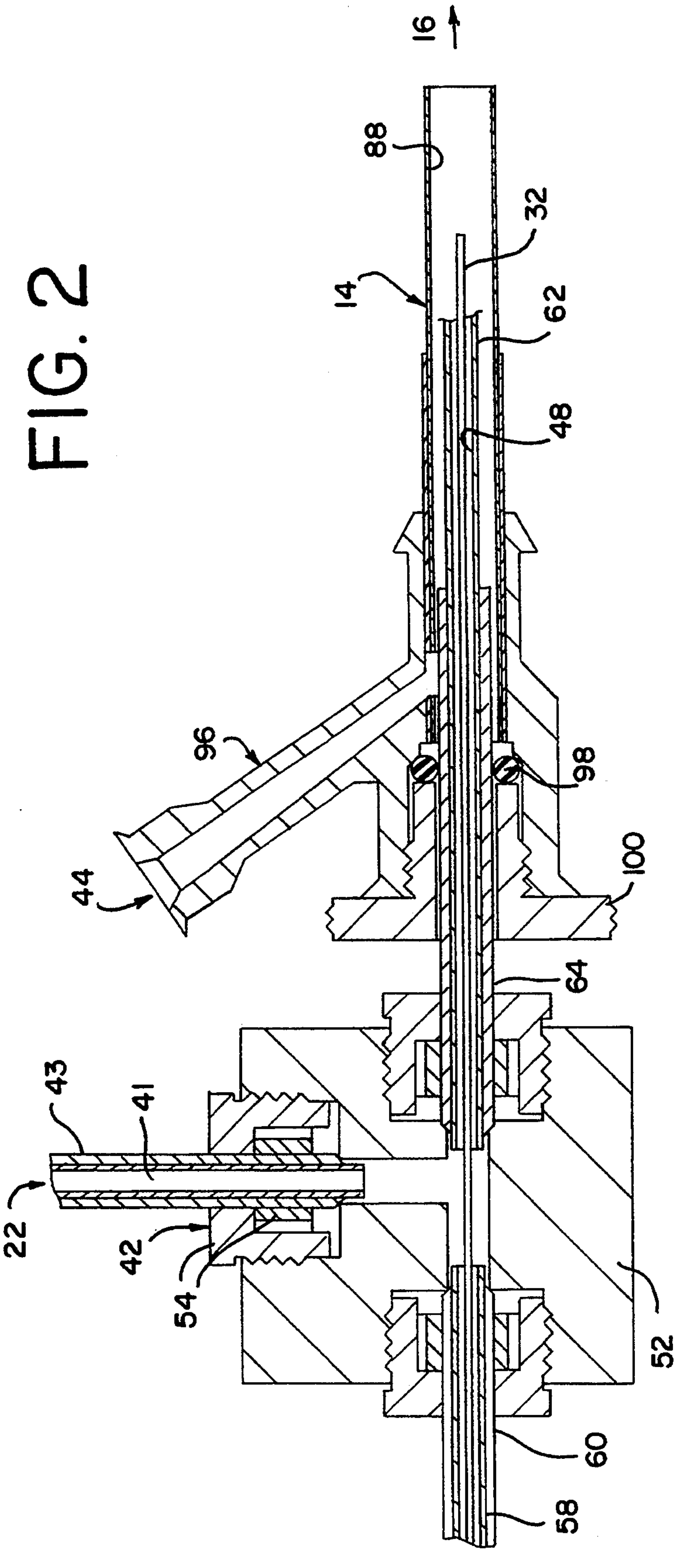
FIG. 2 is a sectional view of a proximal portion of the catheter assembly shown in FIG. 1.

Referring to FIG. 2, in a present embodiment, the first port 42 is comprised of a T-block 52 placed in-line in the first tube 34 of the catheter assembly 14. The T-block 52 may be a commercially available unit purchased from High Pressure Equipment Company, of Erie, Pa. Used in conjunction with the T-block 52 are nuts and glands 54 to form a fluid tight connection to the fluid supply line 43 from the fluid source 22. The T-block 52 connects the fluid supply 22 to a first portion 58 of the supply tube 34 that extends proximally from the T-block and which is located within a spring bushing 60 and to a second portion 62 of the supply tube 34 that extends distally from the T-block and which is located within a wire support bushing 64. It is preferable that the T-block be readily connectable and disconnectable from the pressurized supply line 43 to facilitate use. In further embodiments, the T-block may be manufactured as a custom unit.

At the T-block, fluid pressure is directed both proximally and distally in the supply tube 34. In this embodiment, the fluid 41 moves distally in the lumen 48 of the supply tube 34 to the distal tip 16. In this embodiment, the fluid 41 enters the system under pressure (e.g. 1000 psi or less), as further explained below.

4. Support tube distal portion

Figure 3:
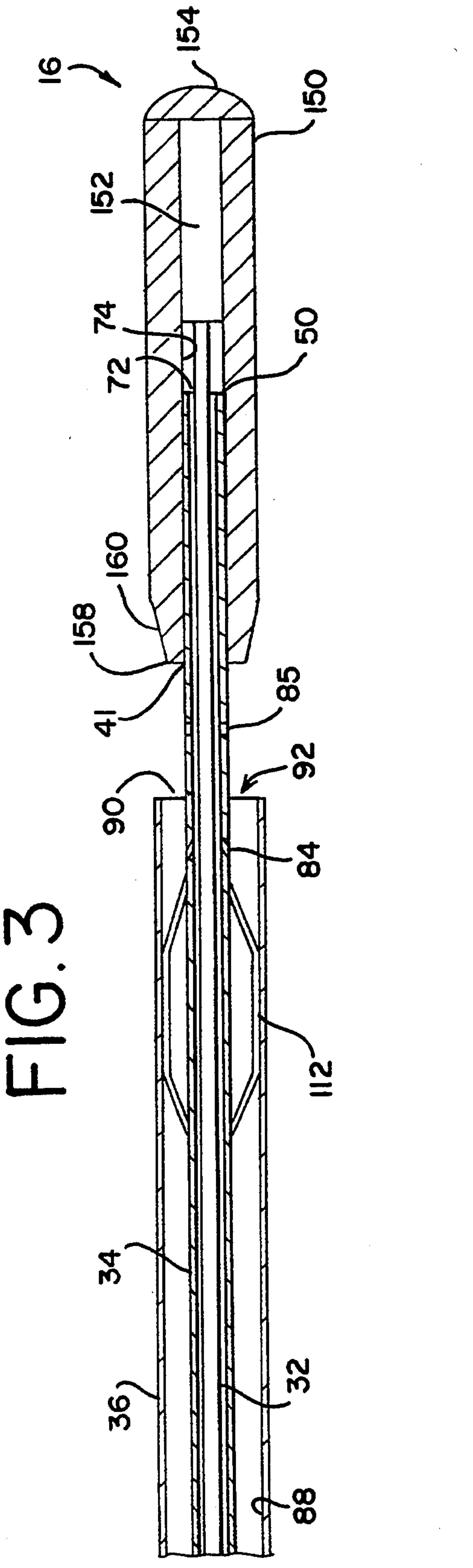
FIG. 3 is a sectional view of a distal portion of the catheter assembly and distal tip shown in FIG. 1.

Referring to FIG. 3, there is depicted the distal end 50 of the supply tube 34 and the distal tip 16. The pressurized fluid 41 is directed from a support tube distal opening 72 located at the distal end 50 of the supply tube 34 to the tip 16. The tip 16 includes a tip channel 74 located internally thereto and open proximally to receive the pressurized fluid 41 and redirect it in a proximal direction.

5. Support tube intermediate portion

In a preferred embodiment, the support tube 34 is comprised of sections along its length having different internal and external diameters. The support tube 34 is provided with sections of different internal and external diameters to allow the flowing fluid medium 41 to retain more of its inherent pressure head by reducing flow losses due to resistance. The Darcy-Weisbach equation demonstrates that as annular clearances are reduced, head loss is increased because the annular clearance is reduced and the fluid velocity is increased through the section to maintain flowrate. Thus the diameter of the support tube 34 is determined for operation at a given driving pressure.

Figure 4A:
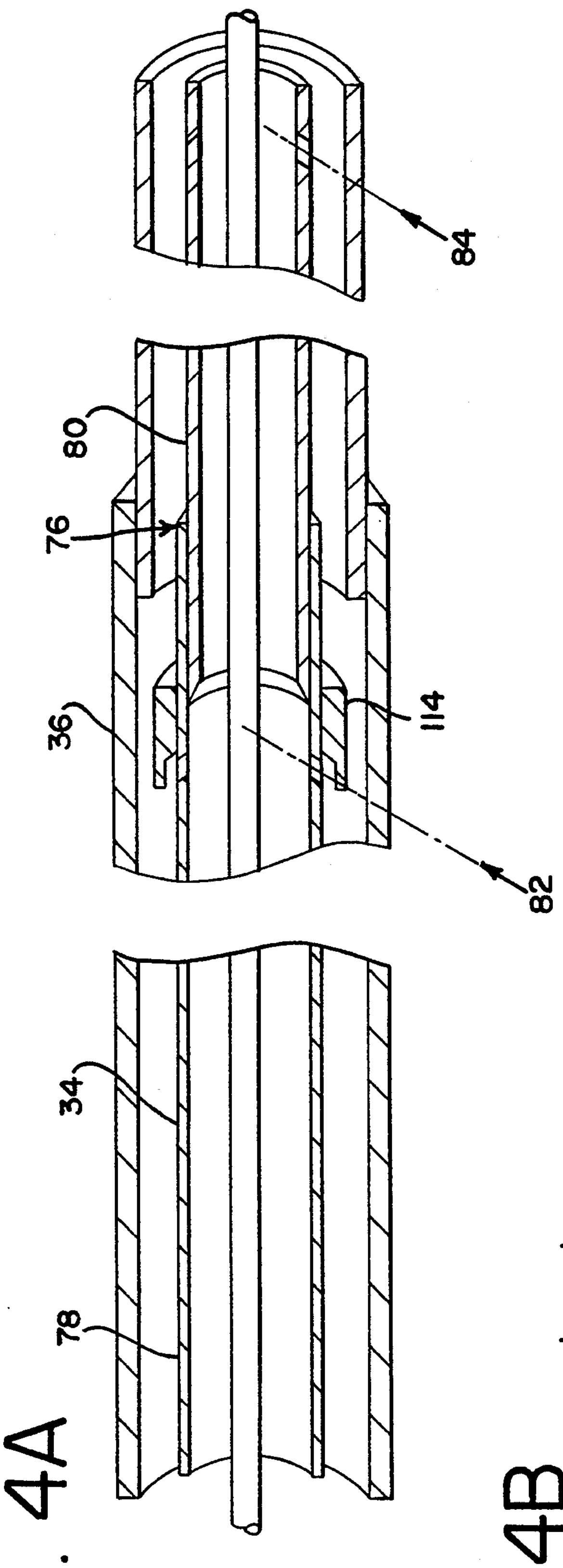
FIG. 4*a* is a sectional view of an intermediate portion of the catheter assembly shown in FIG. 1.

Referring to FIG. 4a, a step down in the diameter of the supply tube 34 occurs at a location 76 approximately 100 cm distally from the distal end of the second port 44 of the catheter assembly. In the present embodiment, this step down is accomplished by forming the support tube of separate sections 78 and 80 fitted into each other and lap soldered together. In a preferred embodiment with an operating pressure of 1000 psi, the inner diameter of the support tube proximal section 78 is 0.026 inches. The inner diameter of the support tube distal section 80 is 0.013 inches. The outer diameter of the support tube proximal section 78 is a constant 0.036 inches. In the distal section 80 of the wire support tube 34, the outer diameter varies. The distal wire support tube outer diameter is 0.025 inches for the first 3.9 inches distally from location 76. Then, the outer diameter of the distal support tube section 80 tapers linearly for 2 inches down to a finished outer diameter of 0.017 inches. In this most distal portion of the wire support tube 34, the wire support tube wall is 0.002 inches thick to provide a desired degree of flexibility and supply pressure. In order to accommodate the differences in diameter between the inner diameter of the proximal section 78 and the outer diameter of the distal support tube section 80, a bushing 81 is positioned between the distal and proximal sections at the connection location 76.

Figure 4B:
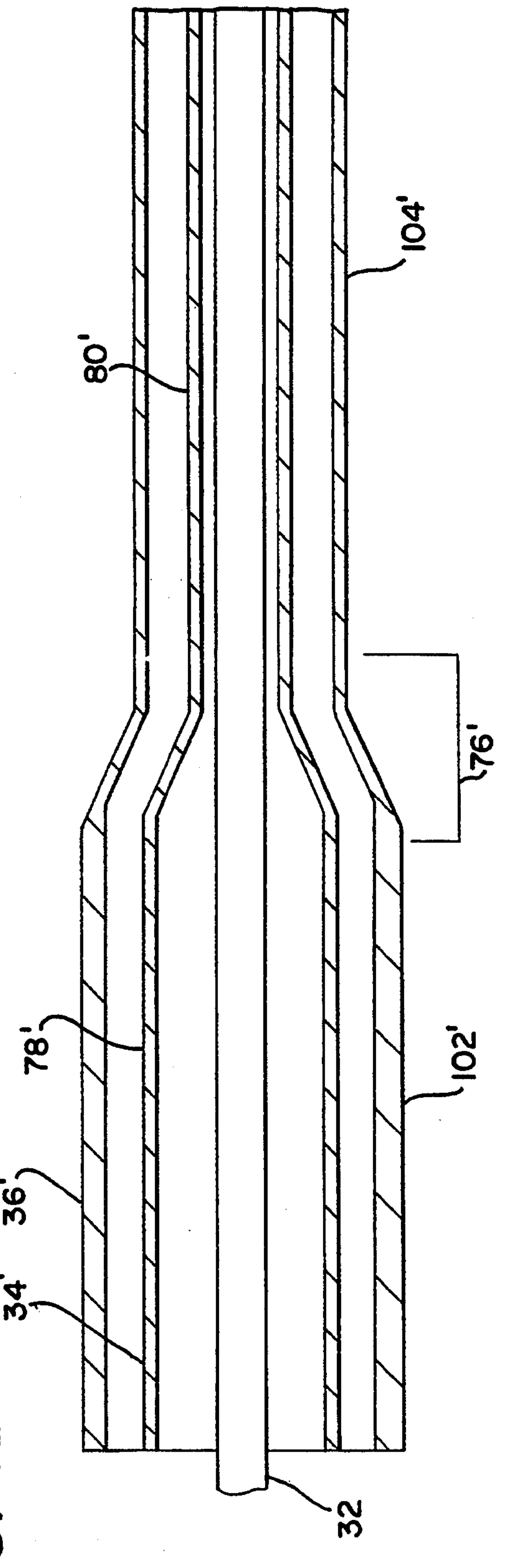
FIG. 4*b* is an alternative embodiment of the intermediate portion of the catheter assembly shown in FIG. 4*a*.

In one embodiment, the proximal and distal sections 78 and 80 of the wire support tube are formed of separate pieces soldered together, however alternatively, a necked tubing would be preferred. The preferred necked configuration is illustrated in FIG. 4b. In FIG. 4b, the support tube 34 would be formed of a single piece of tubing having dimensions corresponding to those of the proximal section 78' and processed, for example by necking, to form the distal section 80' distally of the tapering location 76'. A necked configuration would provide a smoother flow path transition through the catheter assembly thereby reducing flow losses.

The supply tube dimensions are selected in part to provide a specific preferred annular clearance between the inner wall of the supply tube 34 and the core wire 32. The annular clearance between the core wire 32 and the first tube 34 is selected in part to optimize effective performance through various bends that the catheter assembly 14 will undergo during intravascular use. In a present embodiment, the annular clearance is 0.0025 inches in a distal portion and 0.005 inches in a proximal portion. Alternative clearances may be appropriate.

In the present embodiment, the support tube 34 is fabricated of 304 stainless steel although other materials including non-metals having similar properties may also be used. Alternatively, the support tube could be fabricated using fiber composite technology, i.e. the tube could be formed of composite filaments captured in a resin or polymer. Such a construction could increase device pushability, hoop strength, and support to the core wire.

Referring again to FIGS. 3 and 4*a*, in the present embodiment, particle removal ports 82 and 84 are provided in both sections 78 and 80, respectively, of the wire support tube 34. These ports 82 and 84 route the fluid 41 back into the particle removal sheath 36. This redirection by the particle removal ports 82 and 84 allows the kinetic energy of the fluid 41 to become the driving pressure for pushing the fluid and any particulate broken away from the vessel obstruction back to the manifold exhaust port 44. In a preferred embodiment, two sets of ports are incorporated to provide a two stage drawing capability. Primary particle removal is provided by the proximal ports 82 and secondary routing or particle removal initiation is provided by the distal ports 84. In a present embodiment, the proximal ports 82 each have a diameter of 0.010±0.005 inches and the distal ports 84 each have a diameter of 0.003±0.002 inches. In a present embodiment, there are two distal ports and two proximal ports, however, fewer or more ports along the shaft length may be provided and the port size can be modified to adjust flow balance and characteristics.

As a way of improving the pressure balance in the arterial environment during operation and maintaining particle removal flow, distal fluid dispersion orifices 85 may be provided. The dispersion orifices 85 would be located proximal to the proximal end of the distal tip 16 at which the redirected fluid exits the distal tip. The dispersion orifices 85 would be formed to direct fluid normal or slightly proximal to the distal tip axis. The orifices 85 would be located around the periphery of the supply tube 34. The orifice or port size is determined so that a flow balance would be maintained in the artery, thereby preventing collapse of the artery due to a pressure vacuum. The dispersion orifices 85 ports are preferably situated around the periphery of the supply tube 34 so that the proximally directed fluid flow out of the distal tip 16 would be disrupted in select locations corresponding to the locations of the dispersion orifices, but would remain uninterrupted in the locations between adjacent dispersion orifices in order to maintain the particle removal flow path.

6. Particle removal (damping) sheath

Referring to FIGS. 1–4, the second port 44 of the manifold assembly 40 provides the outlet for the discharge of fluid effluent and any particulate attached viscously therein. The second tube 36 (also referred to as the particle removal or damping sheath) is connected at a proximal end 86 thereof to the second port 44. The particle removal sheath 36 extends distally from the second port 44 to the distal portion 26 of the catheter assembly 14. The fluid 41 is withdrawn from the catheter assembly 14 via a particle removal sheath lumen 88 of the particle removal sheath 36. The particle removal sheath 36 extends from the second port 44 to a distal particle removal sheath opening 90 at the distal end 26 of the catheter assembly 14. The particle removal sheath distal opening 90 is located adjacent to the channel 74 of the tip 16, and specifically the particle removal sheath distal opening 90 is located just immediately proximal of the tip channel 74. The particle removal sheath 36 functions to receive and withdraw fluid 41 and any material attached viscously therein from the area at the particle removal sheath distal opening 90. In particular, the particle removal sheath 36 withdraws the fluid 41 supplied via the supply tube 34 that is directed at and redirected by the tip 16. In addition, the particle removal sheath 36 functions to draw particles or material, if any, that may become broken off from the undesired material of the vessel obstruction being treated by the application of energy from the distal tip to the vessel site. It is expected that some, if not most, of such broken off particles or material in a certain size range would tend to be attached viscously in the fluid 41 drawn via the particle removal sheath distal opening 90 though the particle removal sheath 36. In a preferred embodiment, the supply tube 34 is located in the particle removal sheath lumen 88 and is sized to occupy only a portion of the particle removal sheath lumen 88, thereby providing an annular region sufficient to accommodate withdrawal of fluid 41 via the particle removal sheath lumen 88. Accordingly, it is also preferred that the particle removal sheath distal opening 90 is formed by the annular region 92 at the distal end of the particle removal sheath 36 between the inside of the particle removal sheath 36 and the outside of the first (or supply) tube 34.

Referring to FIG. 2, the particle removal sheath 36 terminates proximally at the second port 44. The second port 24 is provided by a Y-manifold 96 connected to the proximal end of the particle removal sheath 36. Inside the Y-manifold 96, the particle removal sheath 36 terminates distal to an O-ring compression seal 98 on the wire support tube 34. The O-ring 98 is retained in the Y-manifold 96 by a compression nut 100. The second port 44 exhausts the withdrawn effluent to a collection pump (not shown) which provides positive pressure or vacuum.

Figure 5:
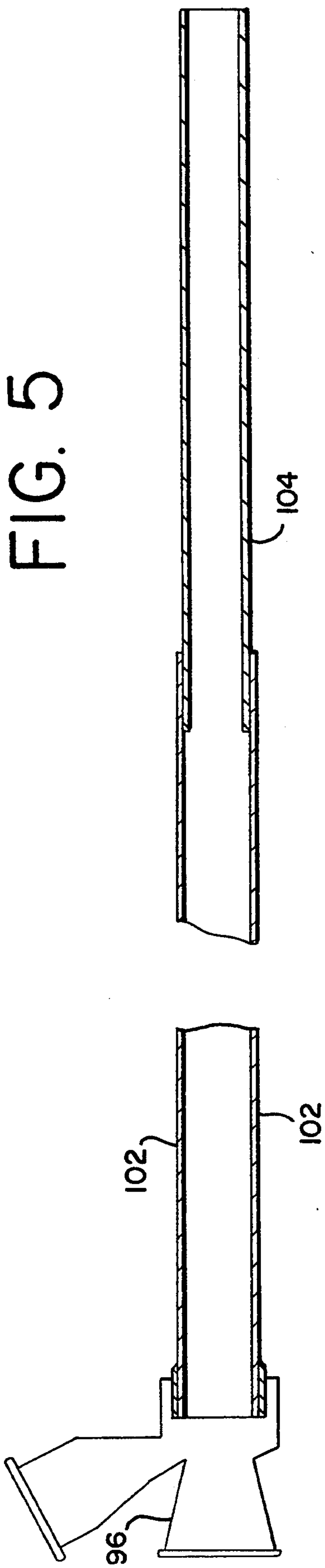
FIG. 5 is a cutaway view of the particle removal sheath portion of the catheter assembly shown in FIG. 1.

Referring to FIG. 5, the particle removal sheath 36 is provided with dimensions to provide for fluid dynamics similar to those of the wire support tube 34 but with substantially lower flow losses through its length. In a present embodiment, the particle removal sheath 36 is formed of a first section 102 connected to the Y-manifold 96. The particle removal sheath 36 may be connected to the Y-manifold 96 by a urethane bond. The particle removal sheath first section 102 is 39.8 inches (101 cm) long and has an inner diameter of 0.042 inches and an outer diameter of 0.052 inches. The particle removal sheath first section 102 connects to a particle removal sheath second section 104. In this embodiment, a second section 104 fits into the first section 102 and extends 13.4 inches (33.9 cm) distally therefrom. The first and second sections 102 and 104 may be connected by a urethane bond. (Instead of forming the particle removal sheath 36 of separate sections, it can also be formed of one piece of tubing and necked or otherwise processed to produce the desired change in profile in a manner similar to that described above with respect to the supply tube and depicted in FIG. 4*b*). The overall length of the particle removal sheath 36 from the distal end of the Y-manifold 96 to the distal end thereof is 53.1 inches. In a preferred embodiment, the particle removal sheath is formed of a single piece of tubing necked to provide the first and second portions 102' and 104' as shown in FIG. 4*b*. The proximal portion 102' has a length of 101 cm with an outer diameter of 0.052 inches and an inner diameter of 0.042 inches. The particle removal sheath second section 104' has a length of 34 cm with an outer diameter of 0.035 inches and an inner diameter of 0.029 inches. As with the supply tube, described above, the second tube may be formed of more than one piece of material and connected together to provide the change in inner and outer diameters, as described above. Such a construction is illustrated in FIGS. 4*a* and 5. If separate pieces are used, the pieces could be connected together by suitable means such as a urethane bond. Additional lengths of tubing may be provided for the purpose of forming an overlapping bond between such separate pieces. An additional length may be provided to connect the proximal end of the second tube into the Y-manifold. In addition, it may be desired to provide the second tube with additional changes in profile to contribute the fluid characteristics, damping, etc.

The distal and proximal sections of the particle removal sheath 36 provide essentially similar functions. Like the supply tube 34, the inner and outer diameters of the particle removal sheath 36 are sized based on fluid dynamic analysis for minimizing pressure drop through each section or portion of the particle removal sheath. The particle removal sheath 36 is also provided with sufficient annular stiffness to prevent collapsing during particle removal flow. A necking process may be used in the construction of the particle removal sheath second section 104 to provide for reduction in diameter and wall thicknesses. In a preferred embodiment, the outer diameter of the distal portion 104 of the particle removal sheath is equal to or less than the outer diameter of the oscillating distal tip 16 to prevent catching of the distal end 90 of the particle removal sheath 36 on lesion material as the tip 16 advances therethrough.

The particle removal sheath 36, in a present embodiment, is constructed from a high density polyethylene (HDPE). HDPE possesses properties considered to be desirable for use as a material for the particle removal sheath. These properties include relatively high stiffness and low coefficient of friction. Other materials for the damping sheath may be used including other plastics or even metals, such as stainless steel or a combination of metal(s) and non-metals, e.g. a composite such as a braided configuration. Alternatively, the damping sheath could be fabricated using fiber composite technology, i.e. the tube could be formed of composite filaments captured in a resin or polymer. Such a construction could increase device pushability, hoop strength, and support.

It is preferred that the particle removal sheath 36 be maintained concentrically disposed about the supply tube 34. Accordingly, a sheath guide 112 may be used. The sheath guide 112 retains the concentricity of the particle removal sheath 36 around the distal supply tube 34. This has the advantage of preventing any side spray or diffusion of the operating fluid 41 when it is redirected proximally into the distal opening 92 due to the particle removal sheath 36 becoming eccentric. The sheath guide 112 is fabricated from radially expanding leaf springs which provide a radial force in an axis-symmetric fashion to produce the proper centering effect.

In addition, in a preferred embodiment, a deflector 114 is provided to additionally support redirection of the fluid leaving the proximal exhaust port 82. The deflector 114 reduces or prevents dispersal when the fluid impacts the inner wall of the particle removal sheath 36. In a present embodiment, the deflector is formed of a tapered piece of stainless steel to reduce flow losses therearound.

In addition to providing an annular passageway for the return effluent particle removal flow, the particle removal sheath or second tube 36 also acts as a damping sheath to reduce or prevent the generation of transverse waves when the core wire 32 is driven in translation. The second tube 36 provides this damping function by providing a frequency dependent stiffness to the catheter assembly. Based on the damping coefficient of the material, the force exerted by the particle removal sheath 36 on the core wire 32 is increased as frequency goes up. The reaction force follows the following relationship:

Damping Force=Damping Coefficient*Velocity

The velocity component in the above equation is determined by the operating frequency of the system. As the velocity is increased, the restraining force is increased linearly. The velocity is the relative velocity between the sheath 36 and the wire support tube 34.

In this embodiment that incorporates fluid particle removal, the return effluent occupying the region between the support tube 34 and the particle removal sheath serves the function of a damping layer. In other embodiments without fluid particle removal, alternative materials may be used to provide for the damping function, as described further below.

7. Core wire generally

Referring again to FIGS. 1 to 4, the catheter assembly 14 also includes the core wire 32. extending therethrough. The core wire 32 is connected at its distal end to the tip 16 and extends from the tip 16 proximally through the first tube lumen 48 of the catheter assembly 14 to the proximal end 30 thereof. In this preferred embodiment, the core wire 32 is sized to occupy only a portion of the first tube lumen 48 thereby allowing an annular region sufficient to accommodate delivery of fluid 41 via the first tube lumen 48 in the annular region. The supply tube distal opening 72 is formed by the annular region at the distal end 50 of the first tube lumen 48 between the inside of the first tube lumen 48 and the core wire 32.

The core wire 32 provides the function of transmitting physical displacement from the proximal end 30 of the catheter assembly 14 to the distal portion 26 and specifically to the tip 16. The transmittance may be accomplished by translation and/or elongation of the core wire 32. In a preferred embodiment, the transmittance is accomplished primarily by translation and secondarily by elongation. In order to perform this function, the core wire 32 is preferably of a biocompatible material possessing a high tensile strength and a high endurance limit. In a present embodiment, high tensile strength stainless steel 304 wire is used. In a present embodiment, the wire used possesses a tensile strength of approximately 300–400 kpsi. In a present embodiment, a commercially available wire is used having a trade name of HYTEN stainless steel wire and produced by Fort Wayne Metal Products, Fort Wayne, Ind. The preferred diameter of the core wire is approximately 0.008 inches, although a wire in the range between 0.005 and 0.010 inches is also considered acceptable. Alternate materials having similar properties may be used for construction of the core wire such as titanium or titanium alloy.

In order to increase axial stiffness (pushability) of the core wire, the core wire may be provided with a larger profile in its proximal portion and a smaller profile in its distal portion. This may be accomplished by providing a core wire with a tapered profile or a profile that is stepped or a combination thereof. The core wire preferably has a small profile distally for increased flexibility in the distal section. Since the catheter assembly is intended for both peripheral and coronary applications, distal flexibility is important. In a present embodiment, the profile of the proximal portion of the core wire is enhanced by the addition of a stainless steel hypotube positioned on the proximal portion of the core wire. The stainless steel hypotube extends over the proximal 39.4 inches of the core wire. The stainless steel hypotube has an outer diameter of 0.015 inches and an inner diameter slightly larger than the diameter of the core wire 32 (i.e. 0.008 inches). The core wire and the hypotube are soldered together so that the effective outer diameter of the core wire in the proximal portion (extending over the proximal 42 inches) is 0.015 inches. The core wire diameter distal of the hypotube is the diameter of the core wire only, i.e. 0.008 inches. Alternatively, instead of being formed of separated pieces, the core wire may be formed of a single piece of wire that is necked down, ground, or otherwise processed to reduce the diameter thereof in a distal portion. In a yet further embodiment, stainless steel or high tensile strength composite fiber coils may be incorporated to the core wire to improve its pushability while retaining flexibility.

In a preferred embodiment, the core wire is coated with a Teflon coating to reduce friction between the wire support tube 34 and the core wire 32. The Teflon coating also contributes to damping of the core wire during oscillation. Other coatings providing low friction may be substituted or used.

In further embodiments, means may be incorporated into the core wire or in the construction thereof, to enhance the resiliency of the core wire. For example, the core wire can be processed with a stress relieving heat treatment for this purpose.

8. Core wire and catheter assembly proximally

Figure 6:
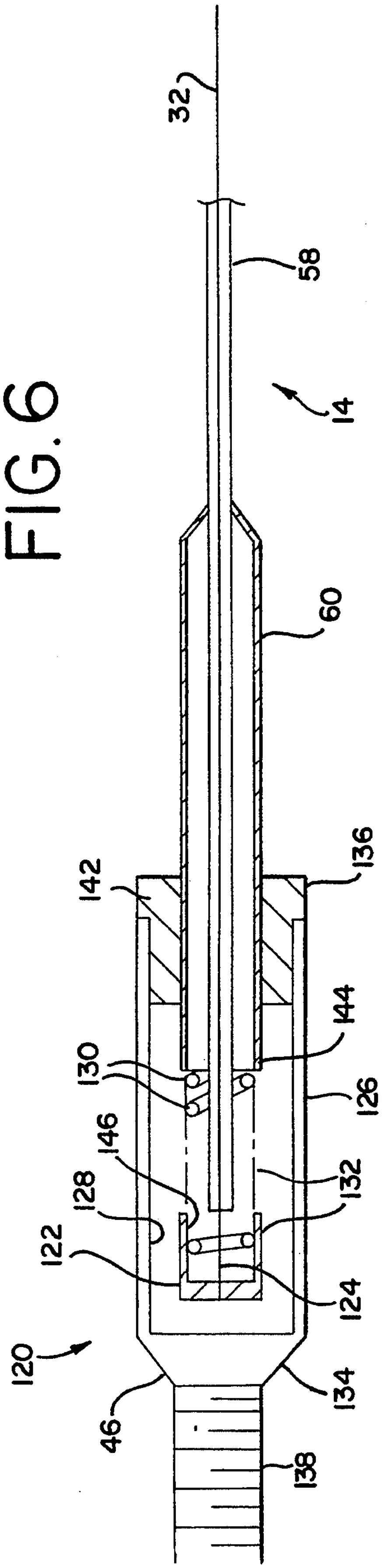
FIG. 6 is a cutaway view of the proximal end of the catheter assembly shown in FIG. 1.

Referring to FIG. 6, there is depicted a most proximal portion 120 of the catheter assembly 14 including the proximal end 46 of the supply tube 34. The driving apparatus 18 (as shown in FIG. 1) imparts movement to the core wire 32 by means of generating an alternating magnetic field that operates on a mass 122 connected to a proximal end 124 of the core wire 32. The proximal end 46 of the supply tube 34 of the catheter assembly 14 includes a pressure vessel housing 126 having therein a cylindrically shaped housing chamber 128. The mass 122 is located in the chamber 128. A spring 130 is adapted to cooperate with the mass 122 and the core wire 32 to form a mass-spring assembly 132, as explained in more detail below. The spring 130 is also located in the housing chamber 128. The chamber 128 is sized to accommodate the axial oscillation of the mass 122 therein. In this embodiment, the chamber 128 is approximately 1.5 inches in length. The driving apparatus 18 generates a magnetic field through the housing 126 that operates on the mass-spring assembly 132.

The housing 126 includes an outer sleeve portion 134 and an outer sleeve bushing portion 136. The outer sleeve portion 134 provides a bearing surface for the magnetic mass 122, isolation between the magnetic mass 122 and the magnetic poles of the driving apparatus 18, and field coupling of the mass (saturation switch), as explained below. The inside diameter of the outer sleeve portion 134 is sized to closely fit to the dimensions of the mass 122. In the present embodiment, the internal diameter of the sleeve portion 134 is 0.210 inches and the external diameter of the mass 122 is 0.200 inches. Thus, in the present embodiment, the radial clearance between the sleeve portion 134 and the mass 122 is 0.005 inches. This clearance gap dimension is determined to provide for efficient transmission of the magnetic field across the gap to the mass 122.

The outer sleeve portion 134 is preferably fabricated from a magnetic material possessing a high permeability and saturation point. In a preferred embodiment, a mild steel is used. Alternatively, stainless steel 416 or other similar materials may be used. The use of a magnetic material allows the flux path from the poles of the driving apparatus 18 to be essentially shunted until the sleeve becomes saturated and the flux is forced through the mass 122. At the time of saturation, the flux is dumped into the mass causing a switch effect on the force level on the mass 122, essentially providing an almost square function forcing curve on the mass 122 which is a desirable result.

The housing 126 also includes a threaded stud 138. The threaded stud 138 is included on an outside proximal end of the sleeve portion 134. The stud 138 functions to provide for tuning of the catheter assembly 14. The sleeve portion 134 is positioned and received into the driving assembly 18, as explained in more detail below. Through the use of the threaded stud 138, the position of the magnetic mass relative to the driving apparatus solenoid poles can be adjusted to provide the desired driving performance. It is preferred that the stud 138 be adjusted to provide maximum displacement of the magnetic mass 122 induced by the magnetic field. Adjustment of the driving apparatus 18 during operation will be further described below.

As stated above, the housing 126 also includes the outer sleeve bushing portion 136. The outer sleeve bushing portion 136 forms the distal portion of the housing 126 and defines the distal wall of the housing chamber 128. The outer sleeve bushing portion 136 fits into an open distal side of the outer sleeve housing portion 134 and includes a shoulder 142 that rests thereupon. The sleeve bushing portion 136 is cylindrically shaped and approximately 0.475 inches in length with the shoulder portion 142 being approximately 0.375 inches long. In the proximal portion of the sleeve bushing portion 136, the outside diameter is sized and adapted to closely fit into the outer sleeve housing portion 134. The outer sleeve bushing portion 136 also defines a cylindrically shaped opening therethrough to receive the spring bushing 60. The outer sleeve bushing portion 136 provides annular spacing between the outer sleeve portion 134 and the spring bushing 60. In addition, to annular spacing, the outer spring bushing portion 136 provides for coaxial assembly of the outer sleeve portion 134 and the spring bushing 60. In a preferred embodiment, the sleeve bushing portion 136 is fabricated from 302 stainless steel and is attached to the outer sleeve portion 134 by means of soldering. Alternative materials and alternative means of connection may be suitable.

As also mentioned above, the spring bushing 60 is mounted in the outer sleeve bushing portion 136. In a present embodiment, the spring bushing 60 is cylindrically shaped and approximately 3 inches long and has an outside diameter of approximately 0.125 inches. The spring bushing 60 defines a cylindrically shaped opening therethrough to receive the proximal portion of the first (or supply) tube 34. A proximal end 144 of the spring bushing 60 provides a mounting surface for a distal end of the spring 130. The spring bushing 60 also provides support to the proximal portion of the supply tube 34 that is received in the opening therein. In a preferred embodiment, the spring bushing 60 is fabricated from 302 stainless steel. Alternatively, other similar materials may be used. In a present embodiment, the spring bushing 60 is soldered to the outer sleeve bushing 136 and the proximal portion of the supply tube 34.

As mentioned above, the mass 122 and the spring 130 are designed to operate together as the mass-spring assembly 132 in conjunction with the driving apparatus 18 to impart the desired oscillation to the wire 32. Therefore, the spring-mass assembly 132 provides for both magnetic circuit coupling of force inducement from the driving apparatus 18 and dynamic inertia for conversion of the spring's potential energy to kinetic energy. The mass 122 is formed of a cylindrically shaped magnetic metal. In a present embodiment, the mass 122 is made of mild steel. This material possesses both desired properties of high magnetic permeability and a high magnetic saturation point material. The mass 122 has a cylindrically shaped recess 146 located therein and oriented in a distal direction to receive the proximal portion of the spring 130. The mass 122 has an outside diameter of 0.200 inches and an internal blind diameter of 0.180 inches. In addition to the recess 146, the mass 122 includes a 0.025 inch center hole for core wire attachment and four peripheral holes (not shown) coaxial therethrough. These latter holes function to improve fluid dynamic flow (whether air or water) around the mass 122.

The spring 130 is connected to the mass 122 inside of the housing 126. The spring 130 provides energy storage for the system 10. For example, in one mode of operation of the driving apparatus 18, the magnetic field generated by the driving apparatus 18 moves the mass 122 proximally. Movement of the mass 122 proximally continues until the dynamic and static forces on the mass 122 are offset by the spring's reaction force due to its attachment to the mass 122 and the spring bushing 60 (i.e. the "reference point" of the system). In a present embodiment, a "music" wire (high tensile strength steel) is used for the spring. The wound spring has an outside diameter of 0.180 inches overall. The spring 130 is preferably fabricated from a material having magnetic properties to contribute to the forcing function applied by the driving apparatus 18 to the magnetic mass. In a present embodiment, the spring 130 is composed of wire having a diameter of 0.032 inches. In a present embodiment, the spring 130 is soldered to both the mass 122 and the spring bushing 60. As mentioned above, the mass 122 includes the cylindrically shaped recess 146 located therein and oriented in a distal direction to receive the proximal portion of the spring 130. When the spring 130 is attached to the magnetic mass 122, the mass recess 146 is preferably partially filled with solder so that some of the proximal spring coils received in the mass recess 146 are fixed, i.e. not active. In a preferred embodiment, four spring coils between the mass 122 and the spring bushing 60 are allowed to remain active, that is, allowed to move during mass oscillation.

9. Distal tip

Referring again to FIG. 3, connected to the distal end 26 of the catheter assembly 14 is the distal tip 16. Specifically, the distal tip 16 is connected to the distal end of the core wire 32. The distal tip 16 includes a distal cap 150 and a distal bushing 152. The cap 150 and bushing 152 are soldered to the core wire 32 for transmission of the core wire movement. The end tip 16 has a distal surface 154 which may possesses a spherical profile, or an other than spherical profile as discussed below.

The end cap 150 extends proximally from the distal bushing 152. The end cap 150 has an inner diameter large enough to accommodate the distal portion and end 50 of the first tube 34 as well as to provide an annular region between the first tube 34 and an inside surface of the end cap 150. The end cap 150 possesses a length such that a proximal end 158 of the end cap 150 is proximal of the distal end 50 of the first tube 34 and distal of the opening 90 of the particle removal sheath 36. In a preferred embodiment, the end cap 150 has an outer diameter of 0.036 inches, an inner diameter of 0.018 inches, and has a length of approximately 0.200 inches. In a preferred embodiment, the proximal end 158 of the end cap 150 is spaced from the opening 90 of the particle removal tube 36 by approximately 0.05 inches during operation. This distance will change of course when the tip is oscillating axially. This distance may also be changed to modify the flow pattern of particulate around the tip. In a preferred embodiment, the outside proximal region of the distal cap 150 is tapered to reduce potential for catching of the proximal edge of the cap on the arterial obstructions during tip oscillation. This tapering 160 may be accomplished through grinding or chemical etching. A taper of approximately 10 degrees is presently used. In a preferred embodiment, the end cap 150 is made of 304 stainless steel.

Located inside the end cap 150 and extending proximally from the end cap tip 122 is a solder joint 162. The solder joint 162 surrounds a most distal portion of the core wire 32 and bonds the core wire to the end cap 150. The core wire 32, a proximal end of the bushing 152 and the end cap 150 define the channel 74 that receives the supply of fluid 41 from the first tube 34 and redirects it proximally. The redirected fluid 41 and viscously attached material are withdrawn from the vascular site via the distal particle removal sheath opening 90. In a preferred embodiment, the end cap solder joint 162 and the bushing 152 occupy approximately 0.05 inches of the end cap 150. In a preferred embodiment, the end cap solder joint 162 is a silver solder compatible with 304 stainless steel and used following generally accepted soldering practices.

Figure 7A:
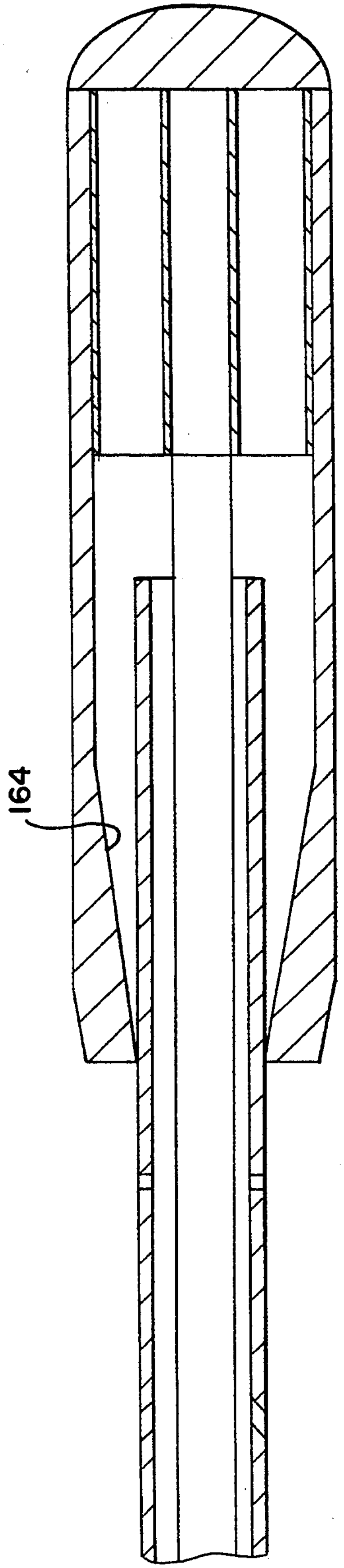
FIGS. 7*a* and 7*b* depict cutaway views of alternative embodiments of the proximal edge of the distal cap shown in FIG. 3.
Figure 7B:
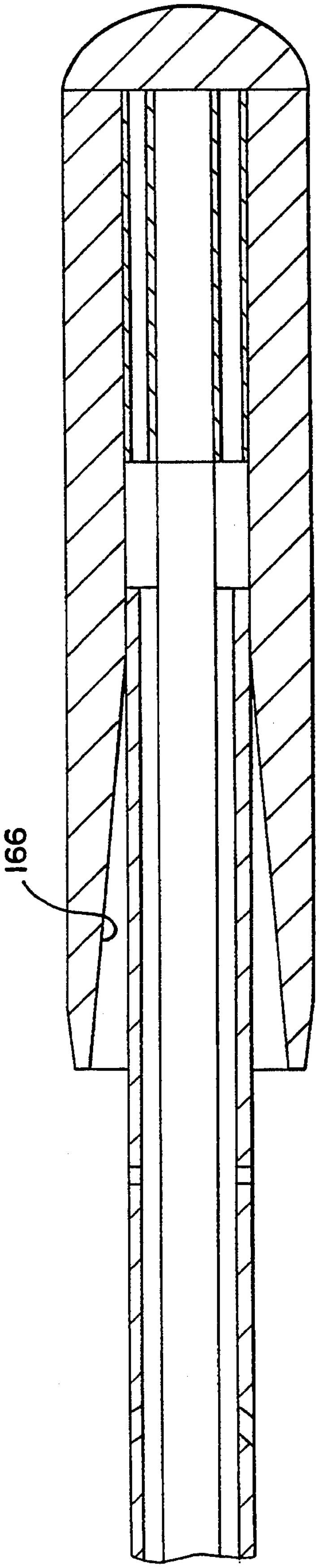

Referring to FIGS. *7a* and *7b*, the inside proximal surface 164 of the end cap 150 can be modified to possess exit flow characteristics to improve particle removal performance. The present embodiment utilizes a straight taper for the proximal inside surface 164. In order to further improve flow attachment, the inside surface 164 can have a reducing taper. Conversely, if a more diffuse fluid flow profile is preferred, an inside surface 166 may possess an expanding taper, as illustrated in FIG. 7*b*. All the taper configurations can be fabricated into the tip using conventional machining processes and deburred with a chemical etch process.

In order to minimize flow losses and mechanical wear losses, all components used for hydraulic conveyance are chemically polished or etched to remove burrs and surface imperfections.

C. DRIVING ELECTRONICS AND HARDWARE

1. Driving Electronics In General

As mentioned above, the driving apparatus 18 is located at and associated with the proximal portion 30 of the catheter assembly 14. The driving apparatus 18 is adapted to impart axial movement (i.e. transmittance) to the core wire 32 located in the catheter assembly 14. According to a first preferred mode of operation, the driving apparatus 18 is specifically adapted to impart a proximally directed force on the core wire 32 which causes oscillation of the core wire due to the action of the spring 130 at the proximal portion of the core wire 32. In an alternative mode of operation, the driving apparatus 18 can be operated to impart a proximally directed (tensioning) force on the core wire while the pressurized fluid 41 imparts a tensioning force upon the tip 16 to move it distally. In this alternative mode of operation, the bushing receives a fluid force that cooperates with the proximal mass-spring assembly 132 to provide for oscillation of the core wire 32.

Referring again to FIG. 6, the core wire 32 is connected at a proximal end 124 thereof to the mass 122. The driving apparatus 18 is adapted to apply its force to the mass 122 of the core wire 32 at a frequency, thereby causing the entire core wire 32, and the tip 16 connected at the distal end thereof, to move in oscillation axially. The frequency and amplitude of the core wire movement is selected to deliver energy to the site at the distal end of the catheter assembly 14, and specifically proximate to the tip 16, for the break up and/or removal of undesired material.

Referring to FIG. 1, the driving apparatus 18 is comprised of a power control system 168 connected to a driving solenoid 169. In a present embodiment, the power control system is comprised of a Peavy CS-800 stereo power amplifier, a BK Precision Model No. 3011B 2 MHz function generator, a Fluke Model No. 77 multimeter, and miscellaneous coaxial cables to route the function generator signal to the amplifier then route the output of the amplifier to the driving solenoid through the multimeter for current monitoring. The driving solenoid is sized to receive the proximal end of the catheter assembly 14 and specifically, the housing 126 containing the spring mass system 132.

2. Dedicated Driving Apparatus

Figure 8:
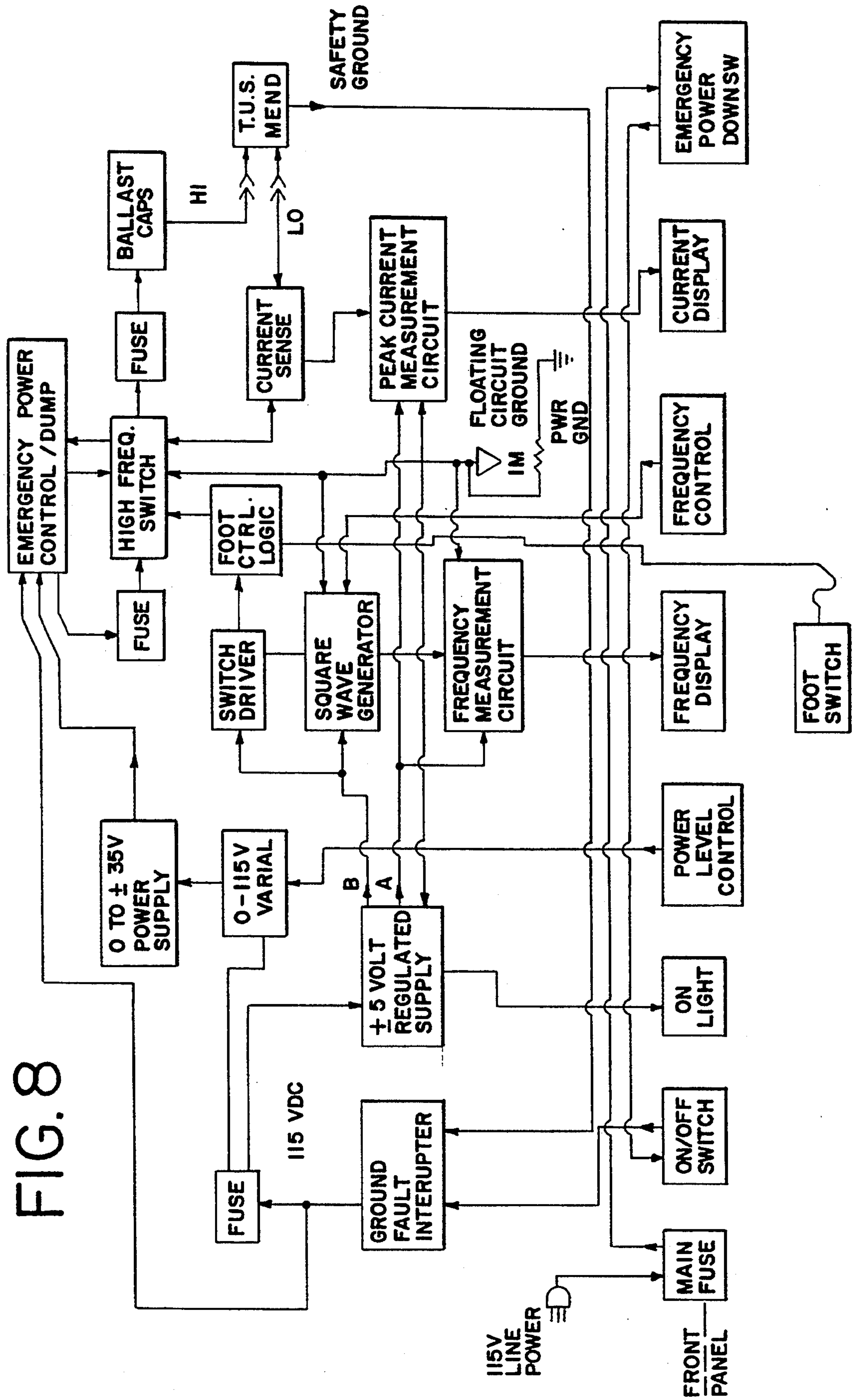
FIG. 8 is a flow chart of a preferred power control system (driving apparatus) for the system 10 of FIG. 1.
Figure 9B:
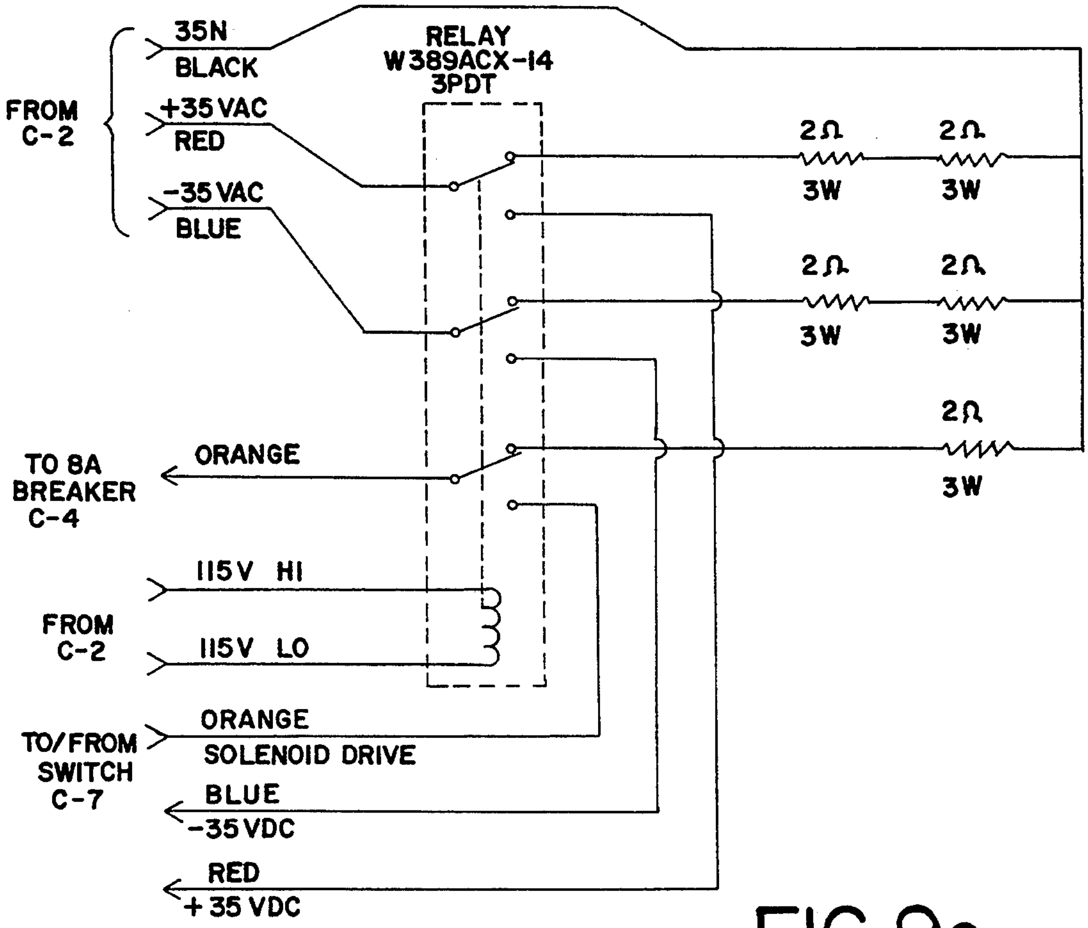
Figure 9C:
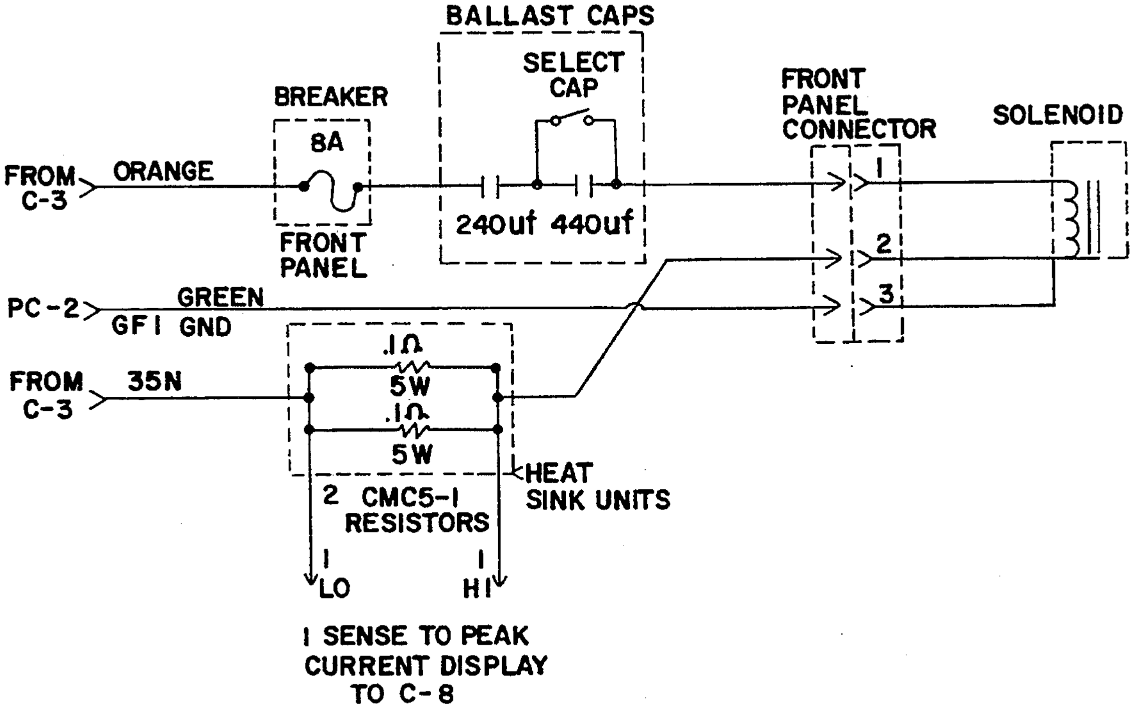
Figure 9D:
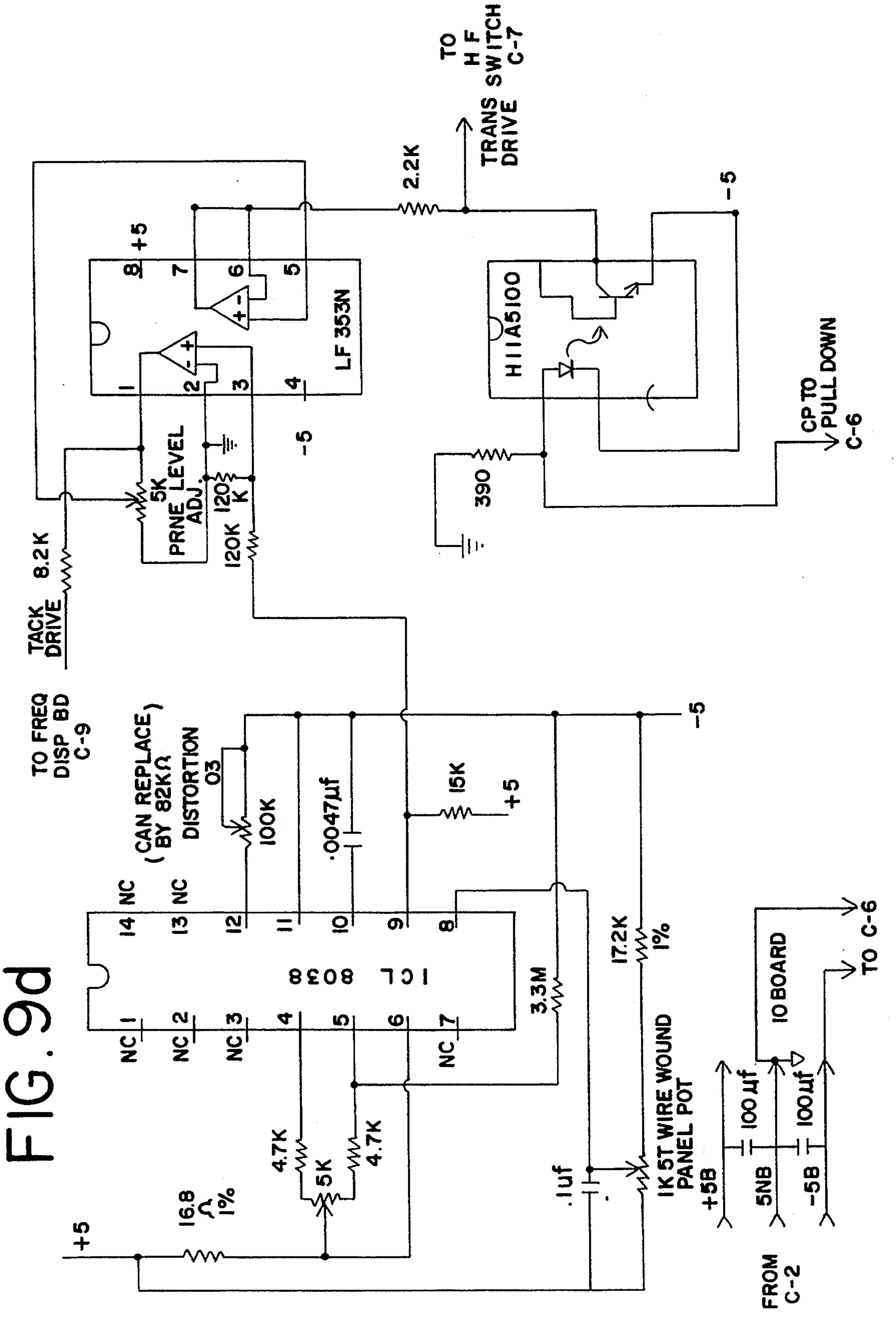
Figure 9E:
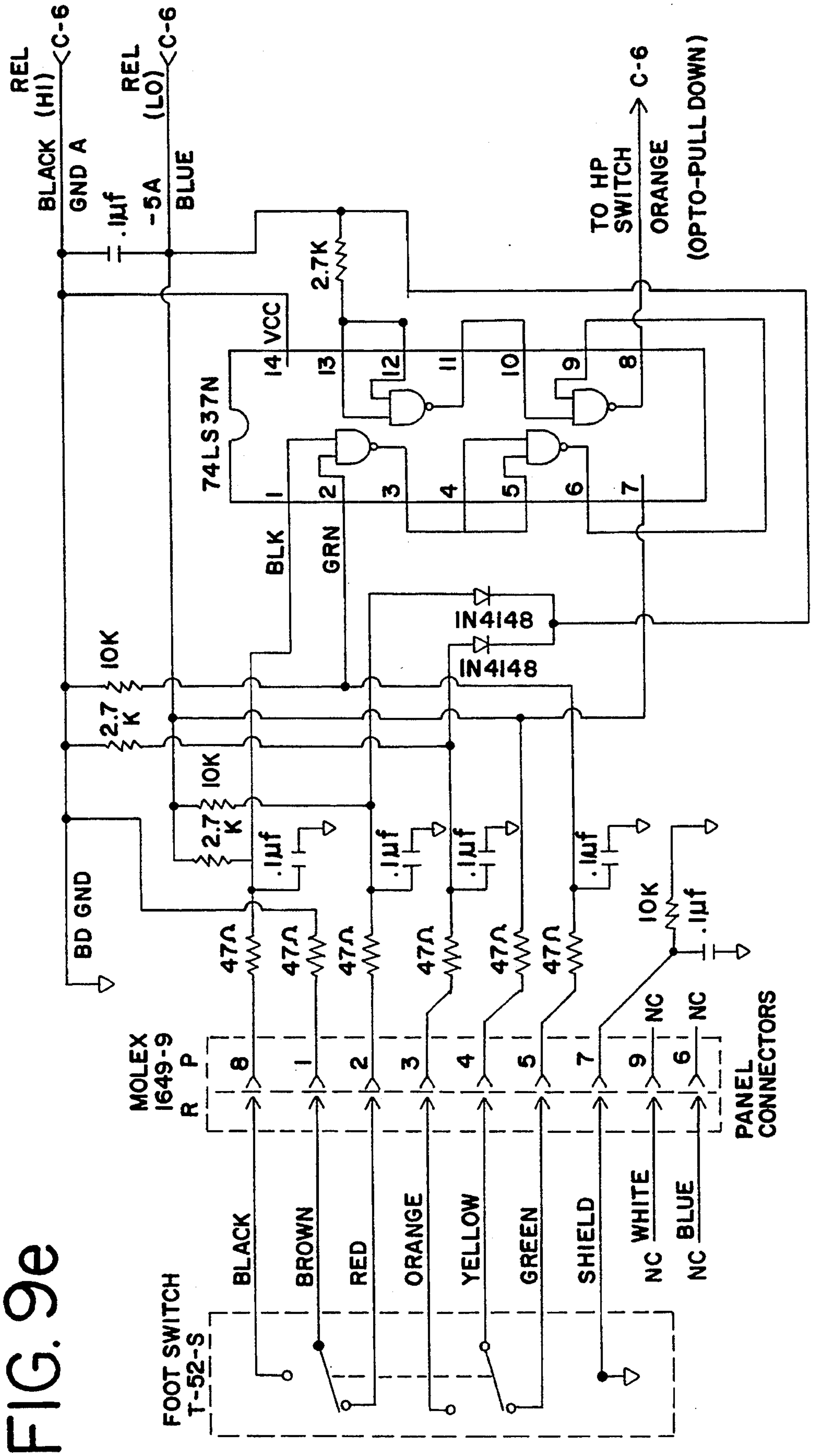
Figure 9F:
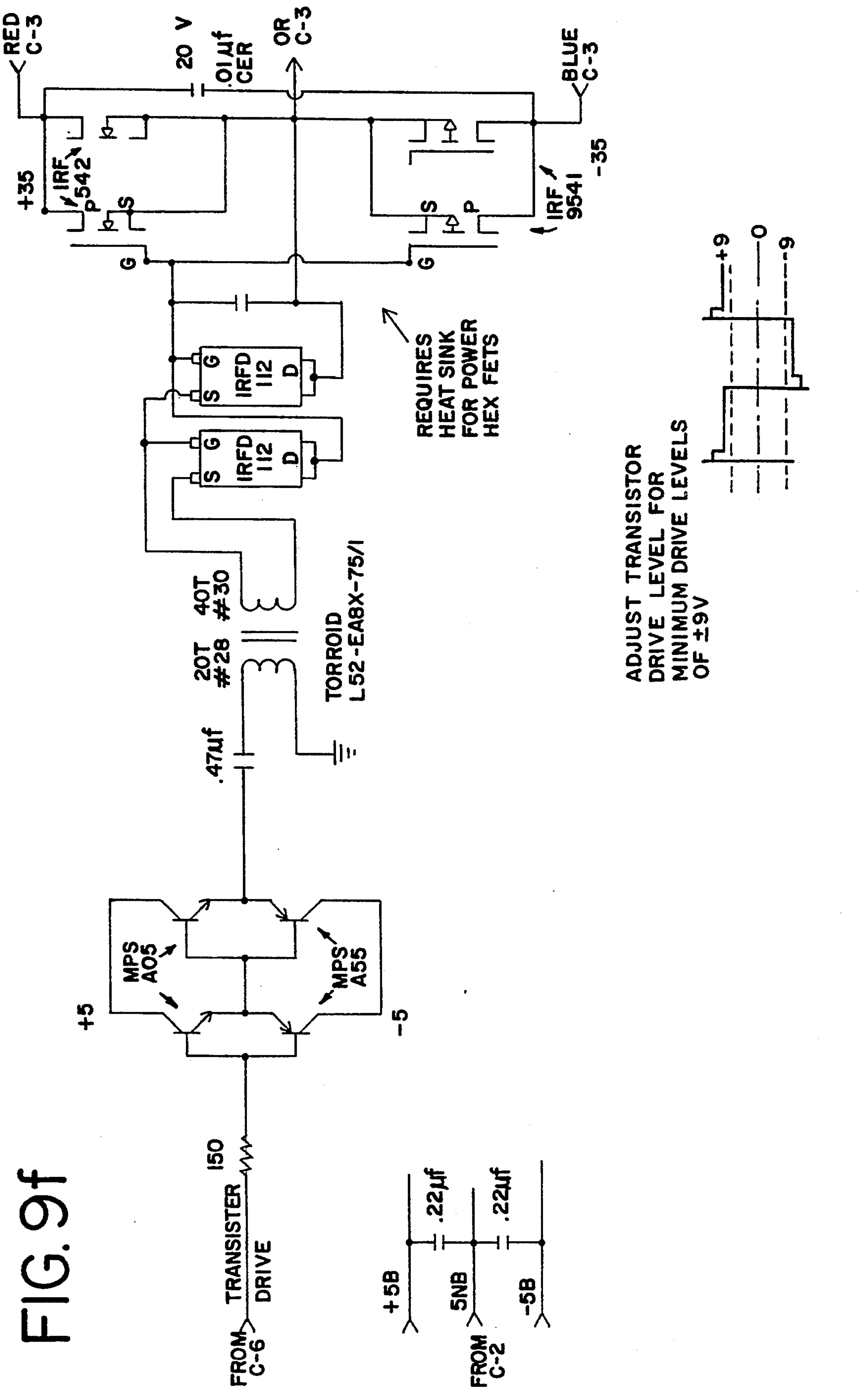
Figure 9G:
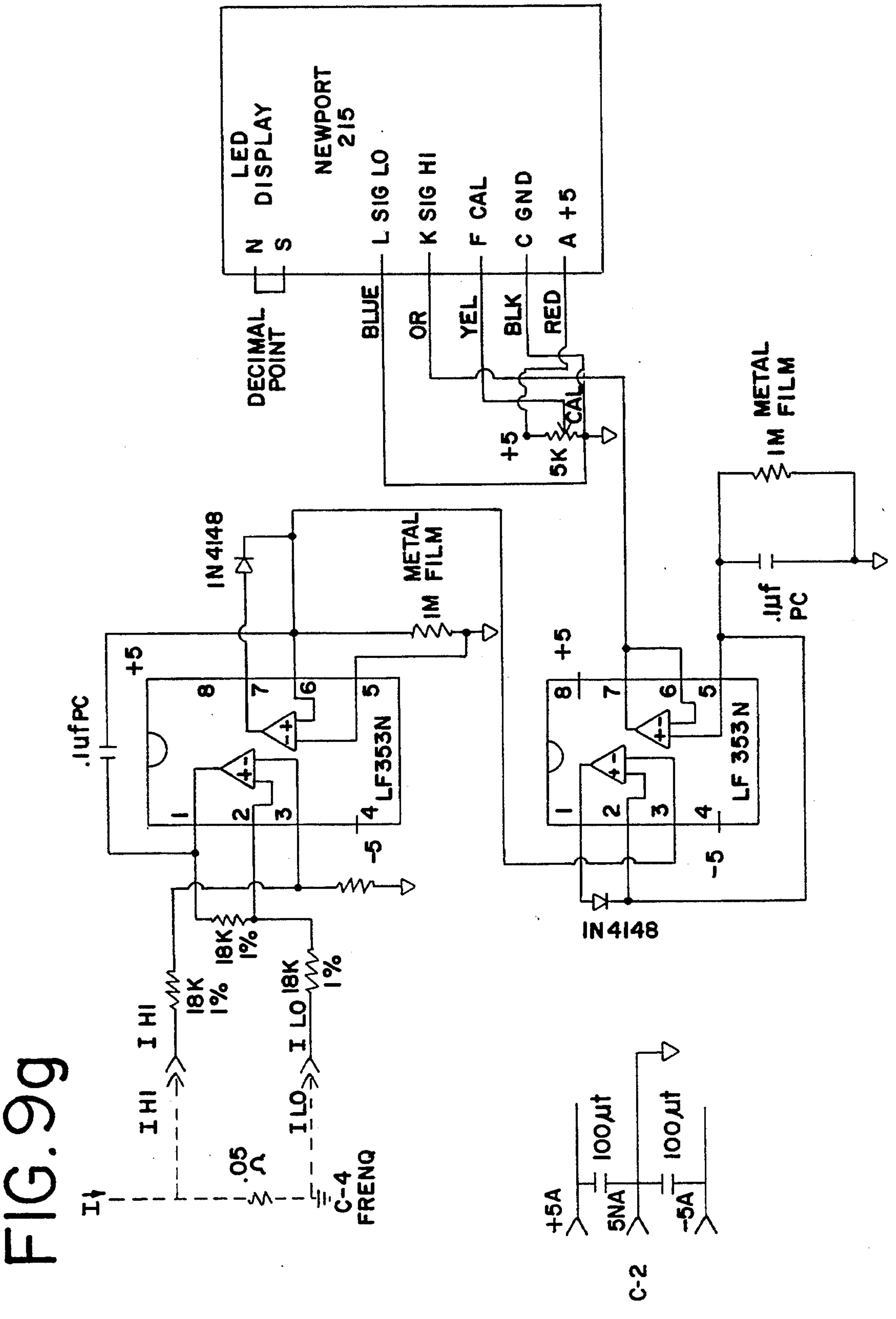
Figure 9H:
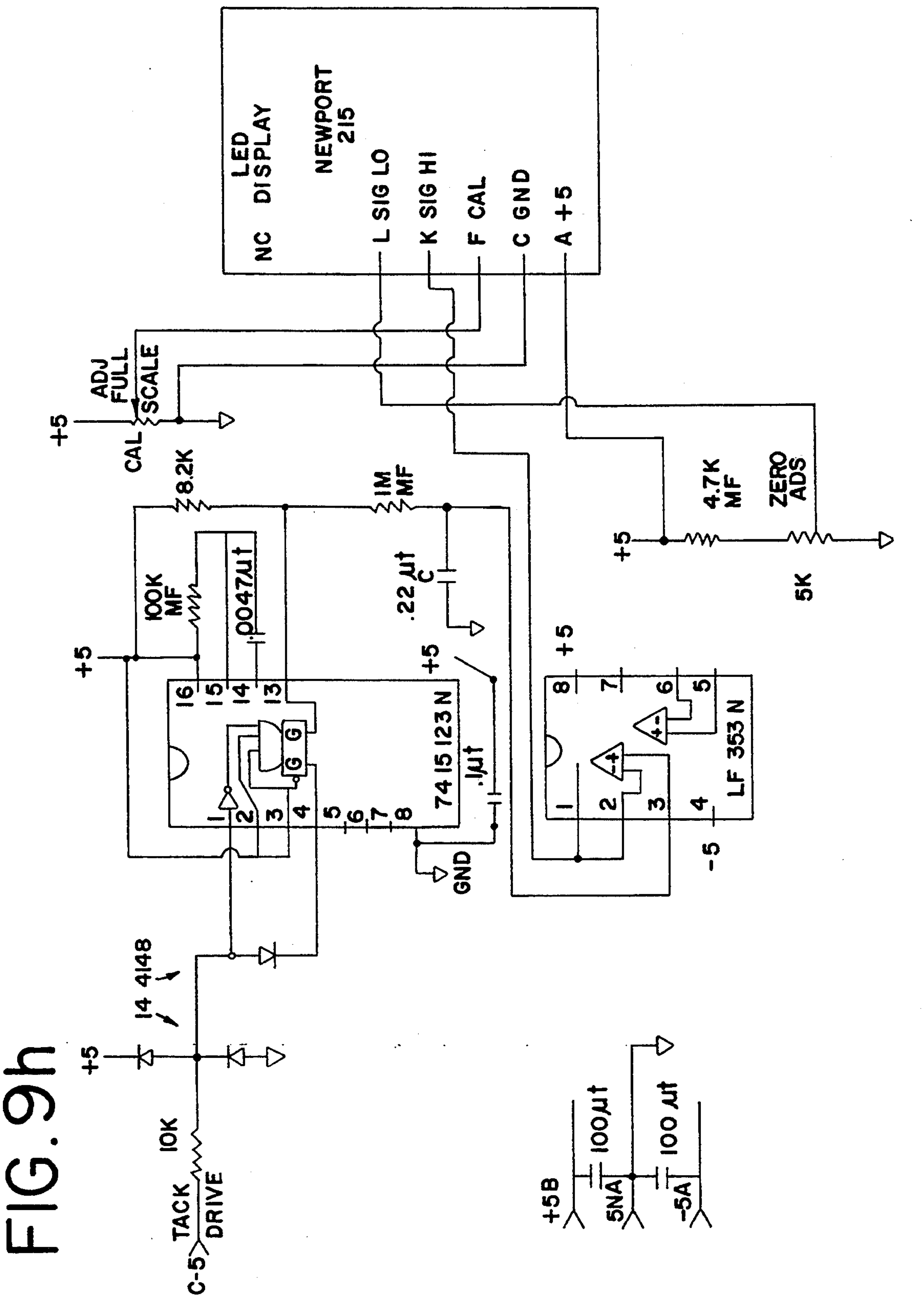

In a preferred embodiment, the above mentioned components used for the power control system are incorporated into a single dedicated system. Such a system is represented by the block diagram of FIG. 8. Circuit diagrams for the power control system shown in FIG. 8 are shown in FIGS. 9*a* to 9*h*. The power control system includes an emergency power control circuit (FIG. 9*b*), a solenoid hook up circuit (FIG. 9*c*), a square wave generator circuit (FIG. 9*d*), a foot control switch circuit (FIG. 9*e*), a high frequency switch (FIG. 9*f*), a peak current display circuit (FIG. 9*g*), and a frequency display circuit (FIG. 9*h*).

3. Solenoid pole configuration and construction

Figure 10:
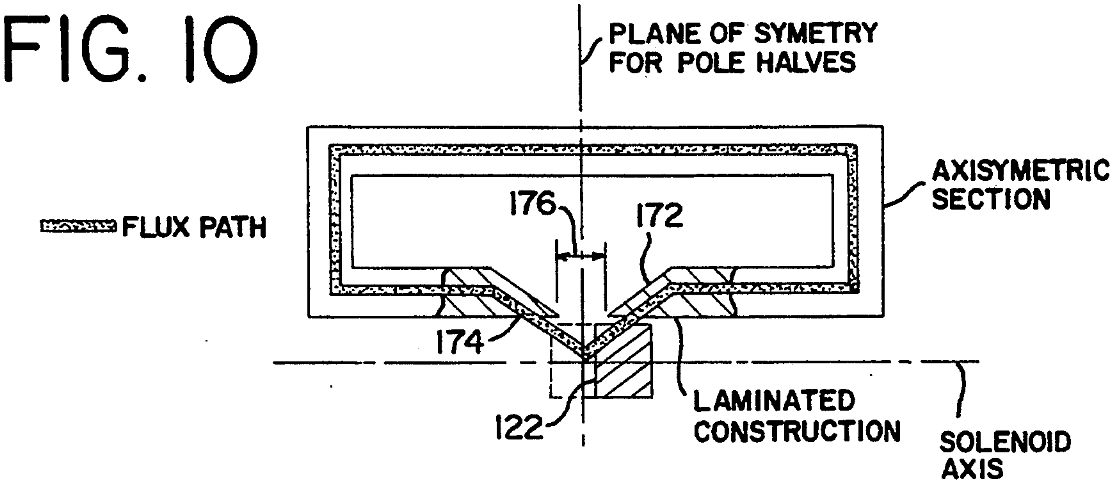
FIG. 10 is a axi-symetric cutaway view of a solenoid pole assembly (with an illustration of the flux path associated therewith) that forms part of the driving apparatus shown in FIG. 1.
Figure 11A:
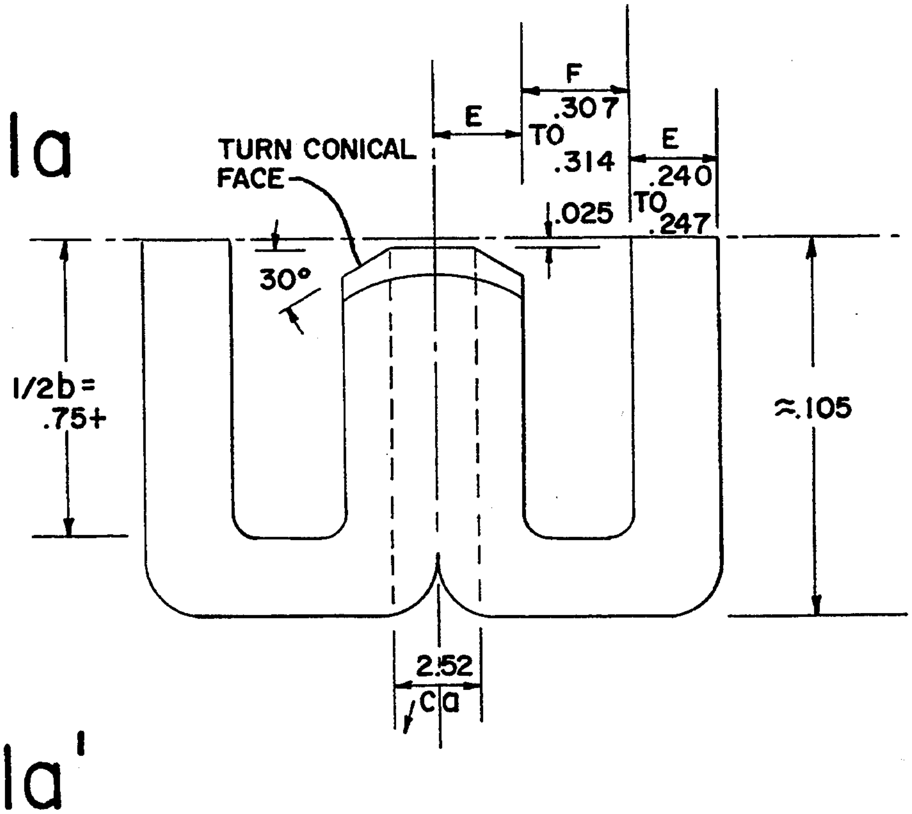
Figure 11A:
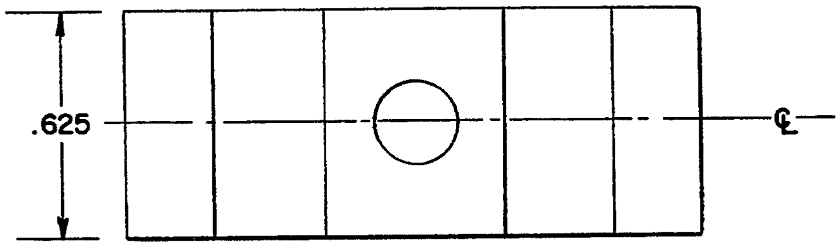
Figure 11B:
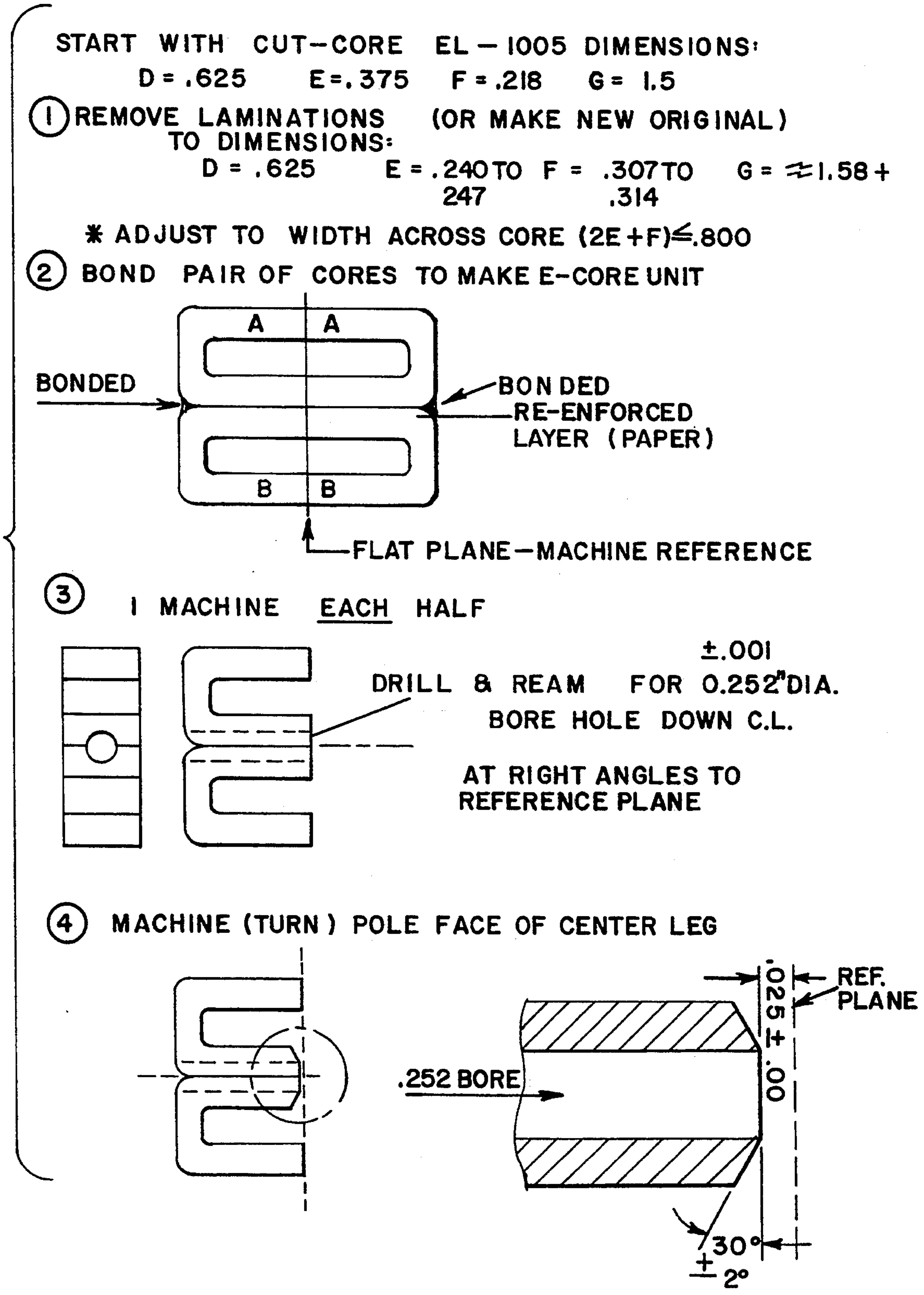

The driving solenoid is comprised of a pair of solenoid poles. Referring to FIG. 10, there is depicted a solenoid pole 170 which can be used for the driving solenoid. The poles are symmetrical and constructed from four U-shaped transformer core assemblies. The core assembly is commercially available from Electro-Core, Washington, Mo., Part Number EL-1005. The cores are constructed by laminating thin magnetic steel layers together to produce a highly permeable core which posses a high saturation point and low eddy current losses (due to lamination construction).

Since the proximal section of the device establishes a magnetic circuit, all component dimensions and tolerances are optimized for overall system performance. Air gaps in the system appear as resistance to the magnetic path and reduce the effectiveness of the magnetic field transfer. The processing steps for construction of the pole pieces and solenoid coil are represented in FIGS. 11*a* to 11*d*.

The faces 172 of the pole pieces are tapered to channel the magnetic flux 174 through the proximal mass thereby improving magnetic coupling with the mass 122. Tapering the pole faces 172 also reduces flux losses across a gap area 176 between the pole faces 172.

The gap 176 between the pole faces is 0.05 inches. This dimension influences the force transferred to the mass 122. Increasing the size of the gap 176 would reduce the force transferred to the mass 122 and thereby result in a decrease of tip displacement; reducing the gap 176 decreases the available mass travel, again resulting in a reduction in tip displacement.

In a preferred embodiment, the solenoid has a body and tuning knob and/or stop, an inner diameter of 0.25 inches to receive the housing 126, and a length of 2.00 inches. In a present embodiment, the driving solenoid requires approximately 200 watts of power at 8 amps.

D. OPERATION

1. Positioning

Referring again to FIG. 1, control and operation of the catheter assembly 14 is effected from the proximal portion 24 located outside of the patient's body. Operation of the system to treat an obstruction at a vessel site involves positioning of the distal portion 26 of the catheter assembly 14 into the patient's vasculature. Positioning may be effected by means and methods which are known to those having skill in the art. For example, the catheter assembly 14 may be positioned percutaneously into the vascular system from an accessible location such as the femoral artery. The positioning of the catheter assembly can be accomplished conventionally through the use of a guide catheter which has been already prepositioned to the obstructed vessel site through the use of a guide wire.

The distal portion of the wire support tube 34 may be formed or bent by the physician-clinician into a slight curvature to allow steering of the tip 16 according to conventional methods known and used with conventional guide wires for intravascular positioning. A slight 'J' can be formed in any variety of radii and locations proximal from the end 16 provided that the bending or curve is at most one inch from the distal tip and that the bend radius is no less than 0.375 inches.

An alternate positioning method would be to implement a quick exchange introducer as described in co-pending application Ser. No. 07/704,828 filed May 23, 1991 the entire disclosure of which is incorporated herein by reference.

2. Driving apparatus operation

Once the catheter 14 has been positioned in the vascular system, the clinician-physician can operate the driving apparatus 18 to impart mechanical energy from the tip 16 by oscillating the core wire with the desired stroke, frequency and power. The driving apparatus 18 is operated to impart axial movement to the proximal portion of the core wire 32. Thus, the operating frequency of the tip 16 is determined by the operating frequency of the driving apparatus 18.

The operating frequency of the system is a function of the system's stiffness (proximal spring stiffness), system mass (proximal mass and core wire), and/or system damping (wire support tube annulus material and clearances). Of these, the most influential component defining the system operational frequency is the system stiffness. Accordingly, in the construction of the mass-spring system 132, materials are selected and processed to provide the appropriate stiffness for the frequency of operation desired. With appropriate selection and construction of materials, the operating frequency can be established at the desired level. In the present embodiment, the operating frequency can be established any point in a range of 100 to 5000 Hz or less.

Tip displacement (amplitude) is a factor in determining a preferred operating frequency for the system. An operating frequency and tip displacement amplitude are preferably selected to yield a tip velocity suitable to recanalize the vessel obstruction by reorganizing the obstructive material or at least temporarily displacing it.

In one preferred mode of operation, the frequency and amplitude are selected to cause cavitation at the tip. Cavitation is favored as a method of disrupting the cellular structure of the obstructive material in the vessel. Studies indicate cavitation generates a tissue dependent disruption, i.e. hard calcified lesions break up readily under low power levels while more compliant healthy arterial tissue remain intact.

Based on fluid dynamics theory and observed arterial pressures and densities, the relationship between frequency and displacement to initiate cavitation has been defined and is shown in FIG. 12. It is observed from the graph of FIG. 12, that as frequency is increased, the required displacement is reduced, therefore high operating frequencies are preferred.

Although operating frequency and amplitude can be selected to induce cavitation at the distal tip 16, another preferred mode of operation is to operate the catheter assembly with a frequency and distal tip displacement less than required to induce cavitation. This low frequency mechanical energy mode has been observed to be very effective in recanalization of occluded vessels. In a present embodiment, a preferred operating frequency of the system is 540 Hz with a tip a peak to peak displacement of 0.100 inches.

Since the operating frequency is proportional to stiffness and inversely proportional to system mass and damping, if a higher frequency is preferred, this can readily be provided by either increasing the stiffness of the spring or decreasing the system mass and damping.

If desired, the peak-to-peak displacement of the tip 16 oscillation can be adjusted down from approximately 0.100 to 0 inches.

In addition to driving frequency and amplitude, another consideration in control system operation and performance relates to the driving system waveform. In the operation of the driving apparatus 18 to oscillate the core wire 32, it is advantageous to minimize the magnetic resistance of the magnetic circuit. Accordingly, the mass 122 is drawn into the center of the magnetic pole gap 176 (of FIG. 10). As the mass 122 is moved from its rest position, a reaction force is generated on the mass by the spring 130. Upon reaching pole center, the magnetic field is removed or shut off and the spring 130 attempts to restore the mass 122 to the rest position. Through the use of digital control in the power circuit of FIG. 8, the magnetic field is energized at a frequency at or below the system's mechanical natural frequency. The process of pulling the mass proximally is repeated at this operating frequency. In one embodiment of operation, this process repeats itself at a frequency of 540 times per second. The driving apparatus 18 and the power sinusoid excitation wave form allows the system to be driven with an electrical signal of 270 Hz, or $\frac{1}{2}$ of the mechanical operational frequency.

Figure 13A:
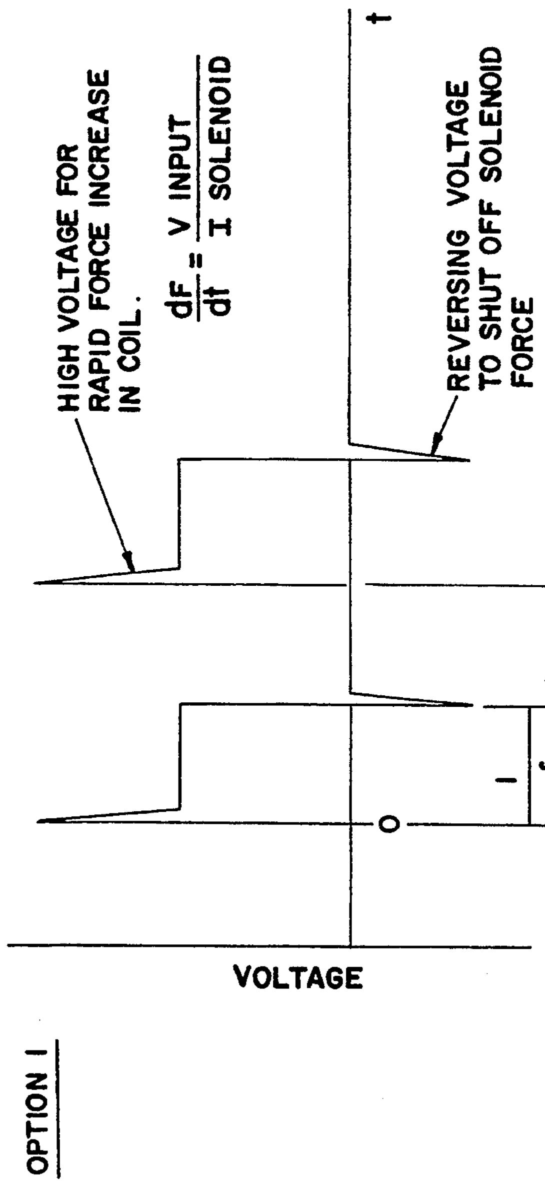
FIGS. 13*a* and 13*b* are graphs illustrating alternative driving waveforms which could be generated by the driving apparatus of FIG. 1 for operating the system.
Figure 13B:
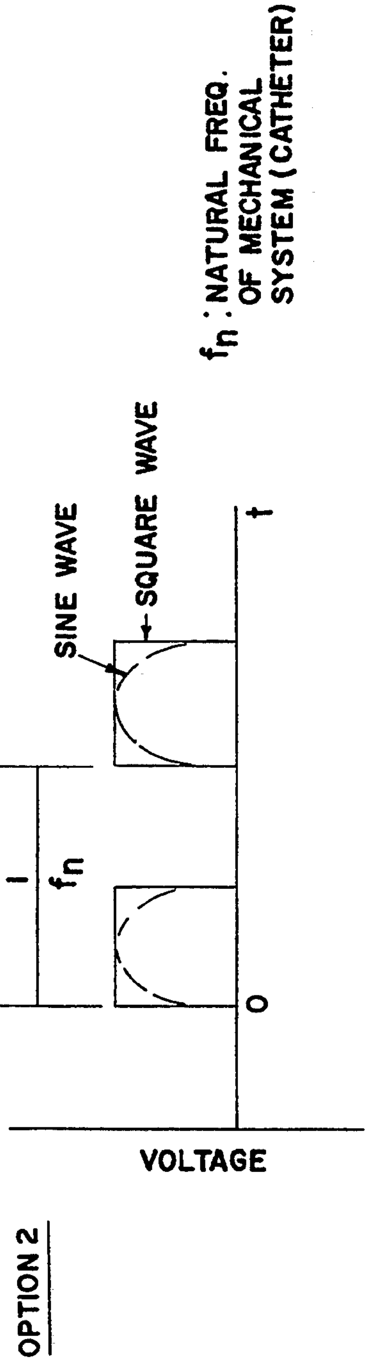

Referring to FIGS. 13*a* and 13*b*, there are graphs of two alternative embodiments of the driving signal that may be output from the driving circuit of FIG. 8 to the solenoid to impart axial movement of the core wire 32. In the first embodiment of operation, the driving signal includes a series of pulses with each pulse having a relatively high initial spike to impart rapid current increase in the coil of the solenoid. The high initial spike is followed by a flat pulse. In this embodiment, each pulse may also include a relatively sharp reverse spike at the end of the pulse to shut off the solenoid force. The waveform depicted in the graph of FIG. 13*b* is another alternative embodiment of the operating mode. The embodiment of FIG. 13*b* shows a driving circuit output signal with a square wave. Application of a force on the proximal end of the core wire to move it distally is provided by the recoil action of the spring in cooperation with the operation of the magnetic oscillation of the proximal mass. In a present embodiment, a sinusoidal wave form is preferred.

In alternative embodiments, the driving apparatus could be operated to move the core wire in a distal direction by application of force on the proximal portion of the wire, instead of relying upon the reaction by the spring to move the core wire distally. Alternatively, the driving apparatus and the spring could combine to move the core wire distally. Alternatively, a distal force may be applied by a combination of both the spring 130 and the driving apparatus.

3. Tip displacement audio feedback

During normal operation of the driving apparatus 18 to impart axial oscillation to the core wire and tip, the system generates an audible sound that is loudest during maximum tip displacement. This coincides with maximum energy delivery to the site of the vessel obstruction. In a preferred mode of operation, the system 10 should be operated at maximum tip displacement to deliver the maximum quantity of energy to the vessel site. Because the system is relatively quiet during operation, the audible feedback from the system may be obscured by ambient noise levels in a typical catheter lab. As a means of providing tip displacement feedback, an audio output from the solenoid is preferably incorporated into the system. The physics of operation of the solenoid produce a variance in the solenoid current requirements as the proximal mass 122 moves through the magnetic gap. Using this current level fluctuation as a control to monitor the oscillation of the proximal mass in the gap and similarly the displacement of the distal tip, a tone signal can be generated whose tone or level would represent tip displacement levels.

An alternate method of displacement monitoring would be to mount a small vibration pickup, similar to a phonographic needle, on the wire support tube 34 and monitor the distal tip energy directly and calibrate its output to tip displacement. Again the pickup's output would be routed to an audio amplifier for generation of a tone which would indicate an acceptable tip displacement.

4. Particle removal in general

According to a further aspect of the present embodiment, there is provided a means for fluid particle removal from the site of the vessel obstruction proximate to the distal tip 16. Fluid removal from the distal tip 16 provides for the removal of particles, such as particles of the undesired material that break away upon application of low frequency mechanical energy or cavitation. This function is provided in part by the flushing action of pressurized fluid 41 as it is applied to the distal tip from the first (or supply) tube 34 and withdrawn by the particle removal sheath 36. This fluid removal action utilizes at least in part the Coanda effect.

The fluid is supplied under pressure to the manifold assembly 42 by the hydraulic pressure source 22. In a preferred embodiment, the hydraulic pressure source 22 is a supply pump that delivers saline fluid at an output rate of up to 200 mL/minute at a pressure that is variable at approximately 1 kpsi or less. The fluid fills the supply tube 34 including the pressure chamber 128 of the housing 126. In the first embodiment, pressurized fluid 41 escapes the supply tube 34 at the distal opening 72 and is directed at the distal tip 16.

The location of the particle removal sheath 36 relative to the distal tip 16 is important for proper particle removal flow performance around the distal tip 16. Referring to FIG. 3, in the present embodiment the distal end of the particle removal sheath 36 is 0.05 inches from the proximal edge 158 of the distal cap 150 during operation. In a present embodiment, the particle removal sheath may be moved relative to the supply tube 34. Movement of the particle removal sheath 36 from the preferred position relative to the supply tube 34 reduces the particle removal effect.

5. Operating pressure

The system 10 with fluid particle removal operates with a preferred inlet 42 pressure of 1000 psi or less. This operating point has been defined by using conventional fluid dynamic relations with preferred geometries in order to attain a mild particle removal effect at the device distal tip. The operating pressure can be increased or decreased based upon the desired particle removal effect. Increasing the pressure results in higher particle removal and more turbulence around the distal tip 16. Conversely, decreasing the operating pressure reduces the amount and severity of particle removal.

The operating pressure is also influenced by the core wire 32 and supply tube 34. If a core wire of a larger dimension is used with a supply tube 34 having the same internal diameter, the required supply pressure increases in order to obtain the same distal exit pressure. The opposite is also true, as the wire size is reduced supply pressure requirements drop.

Depending on the desired particle removal effects and distal fluid mixing, the operational pressure can vary from 500 to 1 kpsi or less.

In an alternative embodiment of the mode of operation, a vacuum could be applied to the second port 44 to reduce the proximal supply pressure requirements while maintaining the same pressure differential between the supply and particle removal ports. Thus, the proximal supply pressure requirement would be reduced to less than 1 kpsi, for example. Application of a proximal vacuum could require a change in the construction of the particulate transmission sheath 36. The sheath 36 would be required to support a high hoop stress and therefore a construction of a hypotube or composite construction may be preferred. In this alternative embodiment of the operating mode, obstruction ablation would be accomplished with the distal tip mechanical movement and a distal orifice. Particulate transmission proximally would be accomplished through the combined efforts of the vacuum and distal return orifices.

6. Operating fluid

At present, saline is the preferred fluid 41 of operation. Saline passes the low viscosity and bio-compatibility required for the system operation. As a possible alternative, a lower viscosity, bio-compatible fluid could be used. In this fashion, a gas such as $CO_2$ could be used. If $CO_2$ were used, it would be important to recover 100% of any $CO_2$ gas input to the system along with any additional fluid attached viscously. The gas, such as $CO_2$, should be bio-diffusible (i.e., quickly absorbed into the blood stream). The gas may be routed through a lubricating reservoir to promote a lubricated wire/support tube interface. Use of a gas may require a tightly controlled distal cap having a proximal annular edge to promote the Coanda effect for flow attachment to the distal wire support tube 34.

7. Mode of particle removal

The present embodiment utilizes two modes of energy transfer for particulate retrieval and removal. The first inherent form of energy into the system is a relatively low velocity, static pressure head flow through the fluid from the hydraulic supply pump 22. As the fluid 41 moves through the system, this low velocity and static pressure is exchanged for a high velocity, low static pressure head energy at the proximal and distal particle removal ports. The ports act as a means of converting any potential head or static head to a kinetic head or velocity head. This conversion to velocity promotes viscous attachment of surrounding particles into the supply fluid and their movement distally with the operating fluid. This viscous attachment yields the distal particle removal zone around the distal tip of the device. As the operating fluid moves proximally, the kinetic head is converted back to a static head pushing the fluid proximally.

8. Supply fluid modulation

In the present embodiment, the supply fluid 41 is stopped during tip oscillation. The fluid 41 can act as a hydraulic damper during supply flow thereby impeding tip oscillation. As a solution the fluid supply may be modulated such that the fluid is supplied at times corresponding to when the driving apparatus is off. This modulation of fluid supply can be accomplished using a manual valve activated either by hand, pneumatics, or electronics to turn the flow on and the magnetic circuit off. The modulation could also be accomplished by an electronic controlling circuit which essentially controls the frequency at which the fluid is turned on and off in sequence with the driving apparatus. Present valved technology would limit the operating frequency of this fluid modulation. Frequencies attainable today at pressures vary from low (less than 1 Hz) using a manual valve to very high (up to 1 Khz) using a bobbin type valve. As an alternative, the fluid supply could be modulated by a solenoid. The fluid modulation solenoid could be continually on and distal mass oscillation would begin when the fluid flow was halted.

In an alternative mode of operation, after crossing a lesion, pressure to balloon during inflation could be modulated to provide a low frequency (0–1000 Hz) balloon profile oscillation.

9. Catheter Exchange

Figure 14:
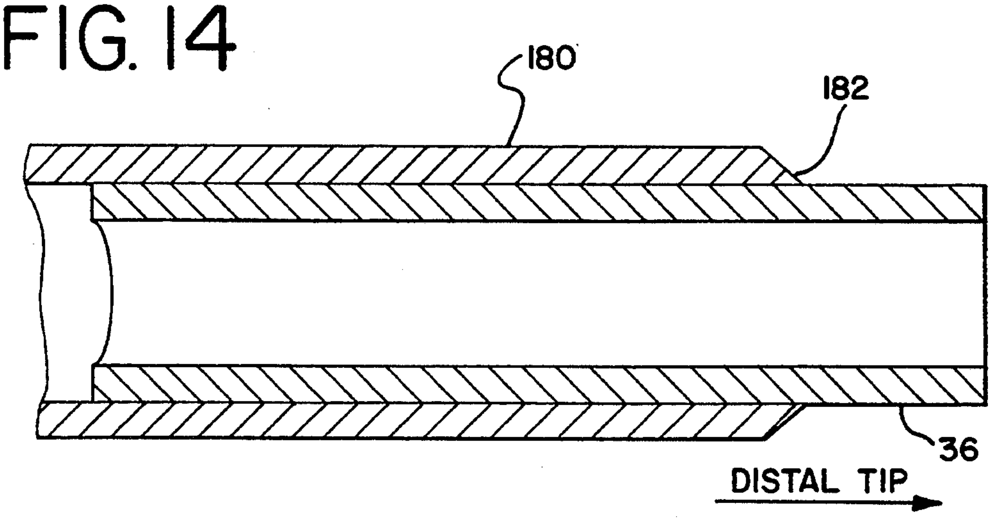
FIG. 14 is a sectional view of a distal portion of an exchange sheath that may be used in conjunction with the embodiment of FIG. 1.

It sometimes is necessary during intravascular procedures to exchange a first intravascular device for another. This may be necessitated by a need for a different device, or for a device with different dimensions or a different bend at the tip. In the present embodiment, the catheter assembly 14 can be exchanged for another, if desired, or for a separate different intravascular device. In order to exchange a first catheter assembly 14 for another, an exchange sheath 180 may be utilized, as illustrated in FIG. 14. The exchange sheath 180 would be positioned over the outside of the catheter assembly 14 before the catheter assembly 14 is positioned intravascularly. Then, the catheter assembly 14 is positioned at the site of the vascular obstruction. A conventional guide catheter may be used for this step. Then, the distal tip is oscillated and the catheter assembly and tip are advanced through the obstruction. Then, the exchange sheath 180 is positioned past the distal tip and over the lesion site after the distal tip 16 has crossed the lesion. Then, the catheter assembly is withdrawn from the exchange sheath and the second intravascular device is positioned through the exchange sheath across the lesion. Then, the exchange sheath may be withdrawn at least partially. The second intravascular device could be a balloon dilation catheter, an atherectomy device, or other therapeutic or diagnostic device, including a second catheter assembly with an oscillating tip. The exchange sheath 180 would preferably have a distal profile with tapered edges 182 to facilitate exchange. The exchange sheath 180 may be formed of high density polyethylene (HDPE) and have an outer diameter of 0.041 inches at the tip and an inner diameter of 0.036 inches. The proximal portion of the exchange sheath 180 may have an outer diameter of 0.059 inches and an inner diameter of 0.053 inches.

10. Alternative method of operation

Although the present embodiment has been described in terms of its utility for the recanalization of an obstructed vessel by the application of low frequency mechanical energy or cavitation to the obstruction, along with removal of broken off particles by viscous attachment by fluid particle removal, there are other ways to use the present embodiment. For example, the present embodiment may be used in conjunction with other therapeutic devices to treat a vessel obstruction. As an example, the present embodiment may be used to establish a passageway through a severely obstructed vessel. Some vessels are so severely obstructed that it is difficult or impossible to get a conventional balloon dilation catheter across the obstruction. The present embodiment could be used to cross such a severely obstructed vessel because the present embodiment is capable of forming a passageway through the obstruction. Then, the catheter assembly of the present embodiment could be removed and a conventional balloon catheter could be installed through the passageway in the obstruction formed by the present embodiment. Then, the balloon catheter could be used to dilate the vessel at the site of the obstruction. Thus, the clinician-physician could be afforded the opportunity to use conventional balloon dilation techniques in locations previously inaccessible to balloon catheters and to choose several different therapies to provide the best treatment as indicated.

II. THE NON-PARTICLE REMOVAL SYSTEM

A. In general

In a first alternative preferred embodiment, the particle removal function may be eliminated. According to this embodiment, i.e. a "dry" system, in some circumstances, it may be considered unnecessary to provide for removal of particles that become broken off of the undesired material. This may be due to the type of material being treated, the location of the material being treated, concurrently administered treatments (i.e. medications) to reduce the likelihood of complications of such broken off particles, or optimization of energy delivery to reduce the likelihood of particulate generation. If such factors indicate that the particle removal function is not necessary, an alternative embodiment of the present invention may be provided in which the catheter assembly 14 does not provide a pressurized fluid via the tube 34 or a return via the second tube 36 for particle removal. In a non-particle removal embodiment, the operation of the system would be similar and treatment would proceed in a manner similar to that of the embodiment with particle removal described above except that there would be no provision for fluid and/or particle removal. Accordingly, in the non-particle removal system there would be no need to provide for the supply pump and fluid outlet.

B. Support tube in the non-particle removal embodiment

In the non-particle removal embodiment, because the annular region between the core wire 32 and the first tube 34 is not used for conveyance of pressurized fluid, it is preferred that a smaller distance be provided between the core wire 32 and the supply tube 34 compared to the system with fluid particle removal. In a preferred embodiment of the non-particle removal system, this may be done by providing a supply tube with smaller dimensions compared to the supply tube in the embodiment with fluid particle removal. In the non-particle removal version, the first tube 34 may be formed of first and second sections as in the particle removal embodiment described above. Referring to FIG. 4a, in the non-particle removal embodiment, the supply tube section 78 has an outer diameter of 0.036 and an inner diameter of 0.026. The supply tube distal section 80 has an outer diameter of 0.014 inches and an inner diameter of 0.007 inches for the proximal 2 cm and an outer diameter of 0.011 inches thereafter. The proximal 1.3 cm of the distal section 80 fits into and therefore overlaps with the proximal section 78. The bushing 81 has dimensions to accommodate the difference in diameters between the proximal and distal sections 78 and 80.

C. Core wire in the non-particle removal embodiment

As in the embodiment with fluid particle removal, in the non-particle removal embodiment, the core wire 32 includes proximal and distal sections having different diameters. In the non-particle removal version, the proximal section of the core wire has an outer diameter of 0.010 inches and a length of 108 cm. In the non-particle removal version, the distal section of the core wire 32 has an outer diameter of 0.005 inches and a length of 35 cm. In a preferred embodiment, the core wire 32 is formed by grinding down a solid wire in the distal portion to form the distal section of reduced diameter.

In a present embodiment of the non-particle removal system, the annular region between the core wire 32 and the supply tube 34 is filled with saline. This is done to reduce friction between the core wire and the first tube 34, to dampen transverse movements of the core wire 32 and supply tube 34 due to core wire oscillations, and to reduce the presence of captivated air in the catheter assembly. Saline is preferred due to its low viscosity and biocompatibility. Other fluids could be used which posses biocompatibility, low viscosity, and good lubrication qualities. The saline is flushed into the area between the core wire 32 and the first tube 34 via the first port 42. Because this embodiment of the present invention without particle removal does not require a fluid pump source 22, the saline may be flushed into the support tube 34 from a syringe.

In addition, to further reduce friction between the core wire 32 and the wire support tube 34, a Teflon liner may be provided on the surface of the core wire 32 and/or a Teflon coating or liner may be applied to the inside surface of the wire support tube 34. In addition to reducing friction with the core wire, the Teflon liner on the inner surface of the support tube 34 provides for damping inside the wire support tube 34 for transverse wave attenuation. Alternatively, a vapor deposition process could be used for adding a low friction bearing surfaces to the inner surface of the wire support tube 34.

In this embodiment of the present invention without fluid particle removal, the ports 82 and 84 and orifices 85 on the first tube would not be required and therefore would be omitted.

D. Damping sheath in non-particle removal embodiment

In this embodiment without fluid particle removal, although the second tube 36 is not required to provide for the particle removal of fluid, the second tube still provides a damping function for the catheter assembly during axial oscillation of the core wire 32 within the first tube 34. In the embodiment with fluid particle removal, the return effluent occupying the volume between the first tube 34 and the second tube 36 contributes to the damping effect. In the embodiment without particle removal, a suitable material may be provided between the first tube 34 and second tube 36 to provide for damping. In one embodiment, the region between the first and the second tubes is filled with contrast fluid or saline. Contrast fluid is preferred because of its higher viscosity as well as its ability to be visible fluoroscopically.

Figure 15:
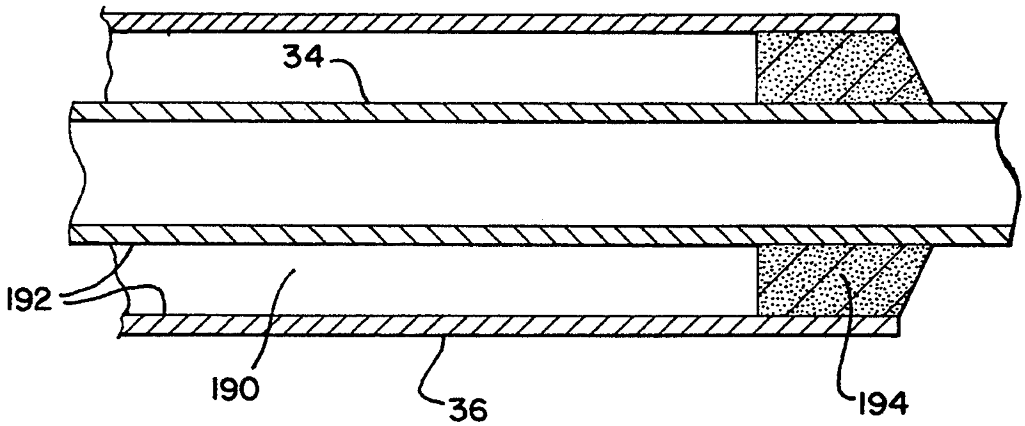
FIG. 15 is a sectional view of an intermediate portion of the catheter assembly of an alternative embodiment of the present system that does not incorporate fluid particle removal.
Figure 16A:
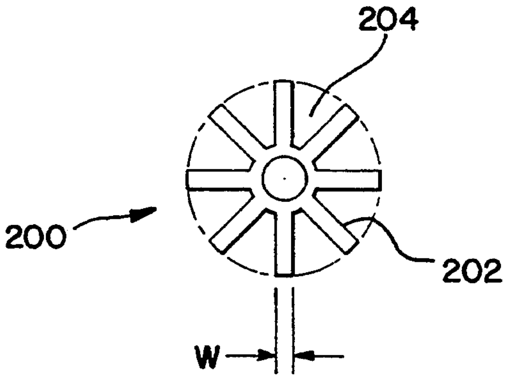
FIGS. 16*a* and 16*b* are cross sectional and longitudinal sectional views of an intermediate portion of the second tube of the catheter assembly of a further alternative embodiment of the present system that does not incorporate fluid particle removal.
Figure 16B:
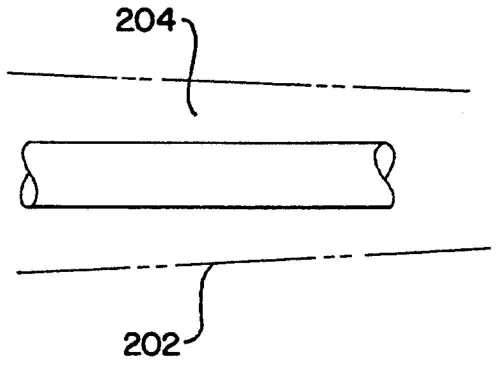

Alternatively, other materials may be used to provide for damping of any transverse movement of the catheter assembly. Referring to FIG. 15, in the embodiment without fluid particle removal, the volume between the first and the second tubes may be occupied by a damping layer 190. In a present embodiment, the conventional constrained damping layer 190 is positioned between the wire support tube 34 and the damping sheath 36. With the appropriate selection of damping material, the inner support tube 34 could be prevented from initiating transverse vibrations induced by high cycle vibrations. Also since the restraining force is frequency dependent, static bending for positioning would realize essentially no increase in device stiffness. The damping layer may be formed of a viscous fluid or a viscoelastic solid. In using a viscous fluid, the viscosity of the constrained damping layer could vary from air with a viscosity of 0.018 cP up to very viscous silicones or other similar materials whose viscosities fall in the order of 70,000,0000 cP. Similarly in using a viscoelastic polymer, such as rubber, the selected material could be selected with moduli of elasticity ranging from 15 to 15000 psi to provide adequate damping and energy adsorption/storage to prevent transverse wave generation. Also, it may be necessary to provide a means for retaining the damping layer material in the volume between the first tube 34 and second tube 36. An adhesive seal 194 may be provided for this purpose.

Because the second tube 36 in the non-particle removal embodiment is not used for the withdrawal of effluent, it may be preferably provided with dimensions especially suitable for the function(s) it performs, e.g. damping. In this embodiment, the second tube 36 has an overall length of 132.7 cm. In the embodiment without particle removal, the second tube 36 may be formed of sections 102 and 104. These sections may be separate pieces that are connected together or alternatively may be formed of a single piece of tubing necked, stretched, or otherwise processed to form sections of different inner and outer diameters. In the non-particle removal embodiment, the proximal section 102 of the second tube 36 has an outer diameter of 0.042 inches, an inner diameter of 0.037 inches, and a length of 98.3 cm. The distal section 104 of the second tube 36 has an outer diameter of 0.024, an inner diameter of 0.014, and a length of 34.4 cm.

III. OTHER ALTERNATIVE EMBODIMENTS

A. Damping Sheath Alternative Embodiments

1. Splines

In the above described embodiments, damping was provided by the second tube 36 and a material between the second tube 36 and the first tube 34. In the system with particle removal, damping was provided, in part, by the return effluent and in the non-particle removal system damping was provided, in part, by other materials. In an alternative embodiment, the wire support tube 34 could be encapsulated or formed in a polymeric tube 200 that provides damping and stiffness through the use of longitudinal splines 202 running the length of the catheter assembly. The polymeric tube 200 would replace and serve some of the same functions as the second tube 36 described in the embodiments above. The splines 202 would be tapered in diameter as the distal portion of the shaft is reached to improve distal flexibility. The use of splines 202 would allow an increase in the proximal stiffness of the device while maintaining a substantial area 204 for contrast flow around the device during angiography operation. The outside diameter of the splines 202 would be sized such that the device could be used in a conventional 8 Fr guide catheter. The splines 202 may be incorporated into the inside wall of the second tube 36 or alternatively may be used as a substitute for the second tube 36 in a device that does not include a fluid particle removal system.

In an alternative in which the splines 202 replace the second tube 36, the conventional guide catheter used for positioning the device may be used as well for additional structural support. The guide catheter will provide a support against which the spline configuration of the polymeric tube can be disposed against during operation. The spline configuration of the polymeric tube 200 provides an adequate room for contrast fluid to flow around the spline configuration to the lesion site when it is in the guide catheter during angiography.

2. Rheological Fluid

Referring again to FIG. 15, in yet a further alternative embodiment, a rheological fluid could be used as the damping layer material 190. This alternative would provide for increasing device stiffness and maintaining flexibility during positioning. The rheological fluid would be located in the annulus between the wire support tube 34 and the damping sheath 36. A rheological fluid posseses the feature of essentially changing phase, from fluid to solid, when exposed to an electrical field. When the electrical field is removed the material returns to its original fluid state.

Incorporating this feature into the damping sheath 36 would allow the catheter assembly to be located within the vasculature and then to be fixed using an electrical field providing a stiff outer member during device operation for improved wire translation. The location of the rheological fluid annulus in terms of distal position could be any length based on the device performance requirements and required longitudinal stiffening. For use of the rheological fluid, a metalized surface 192 on both the wire support tube 34 and the damping sheath 36 would be required to establish the appropriate electric field across the fluid medium 190. This would be similar to a coaxial capacitor.

B. Distal Cap Alternative Embodiments

Figure 17:
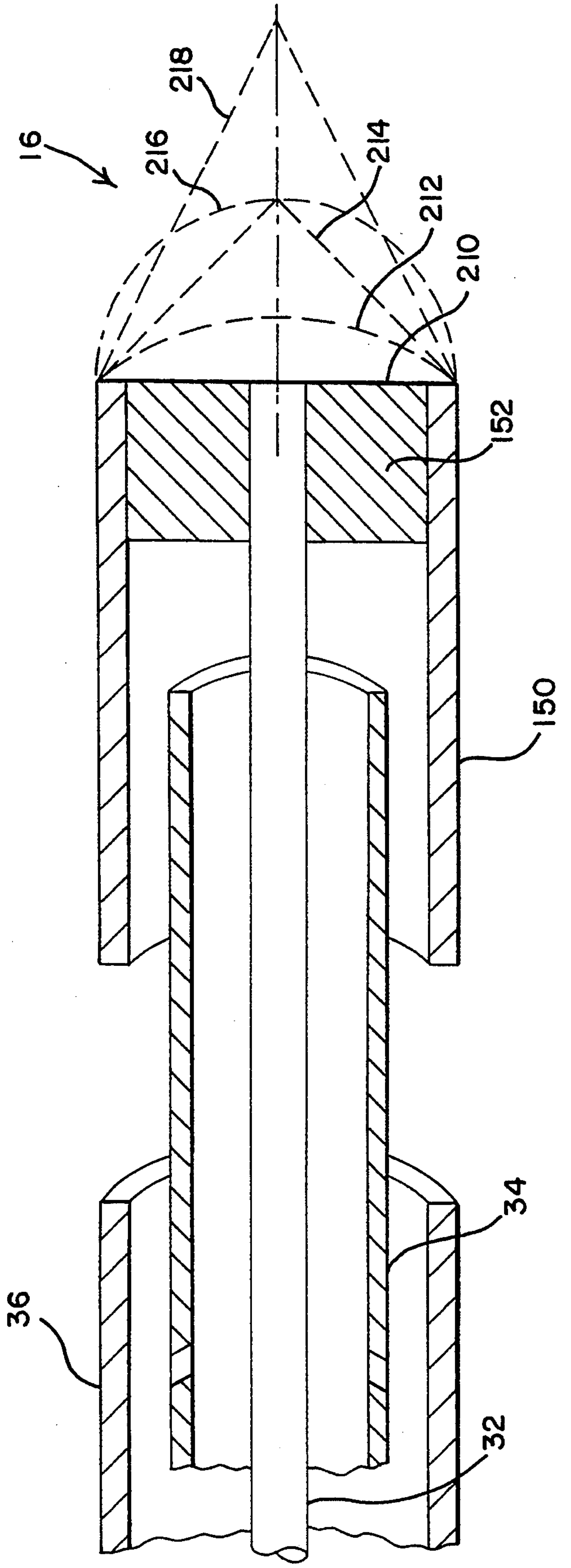
FIG. 17 is a sectional view of a distal portion of the catheter assembly of FIG. 1 illustrating alternative embodiments of the profile of the end cap tip.

Referring to FIG. 17, there are depicted alternative embodiments for the profile of the surface 154 of the distal tip 16. Alternative profiles include flat 210, slight curvature 212, slight linear taper 214, spherical 216 or large linear taper 218. Each of these profiles may be particularly suitable depending upon the selected operating speed, displacement, and type of material being recanalized. In present embodiments, the spherical face 216 and the flat face 210 are preferred due to their leading edges which provide a location for flow separation during the back stroke of the distal tip to induce cavitation. The linear taper 214 or conical face 218 may be preferred in terms of greater penetration when operating below the cavitation frequency.

Figure 18A:
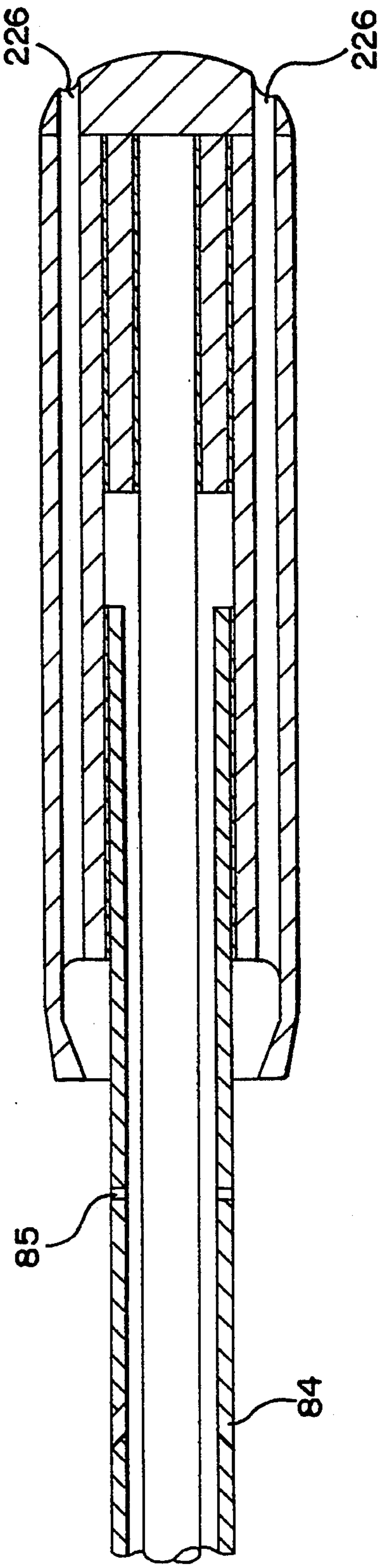
FIGS. 18*a* and 18*b* depict views of alternative embodiments of the distal cap.
Figure 18B:
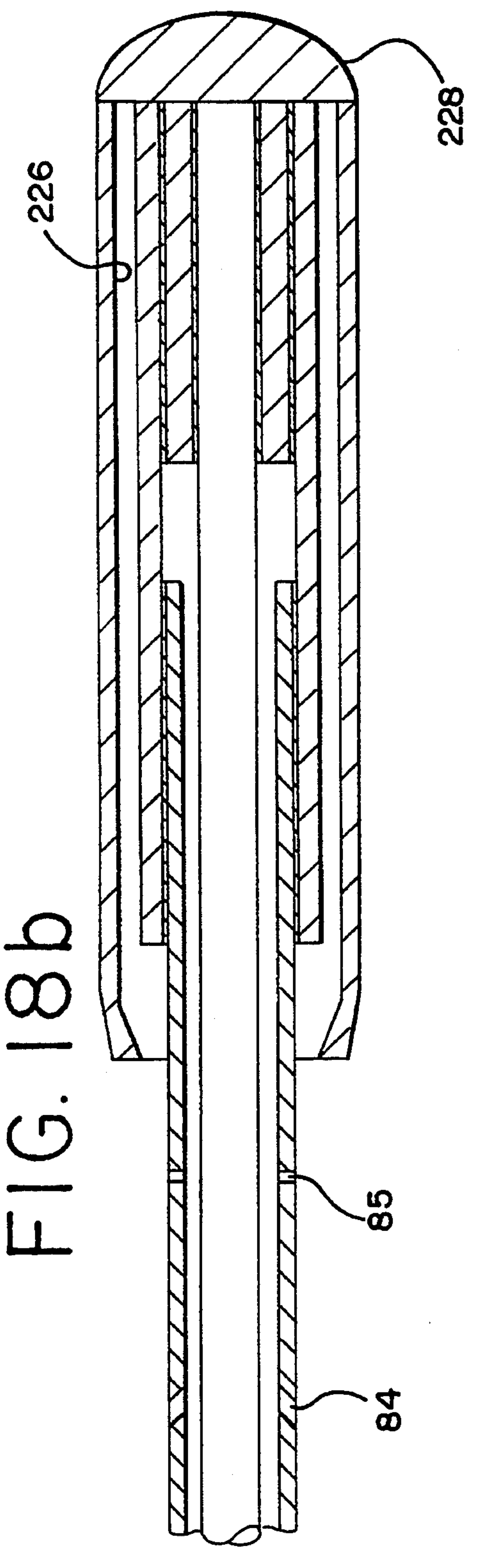

Referring to FIGS. 18*a* and 18*b*, there are depicted alternative embodiments of the distal tip 16 having incorporated therein means for reducing the local pressure field around the distal tip 16. In FIG. 18*a*, bleed ports 226 extending through the distal surface 154 of the tip are incorporated through the distal tip 16. In FIG. 18*b*, a permeable member 228 is incorporated in addition to bleed ports 226. The permeable member 228 extends over the bleed ports 226 through the distal tip 16. Bleed ports 226 or the permeable member 228 are incorporated into the distal tip 16 to promote a local low pressure field. In effect the bleed ports 226 and permeable member 228 act as pressure taps from the relatively high pressure blood field outside the tip to the relatively low pressure field at the distal return orifice. These alternatives would be most effective in an embodiment that did not possess any ports, e.g. 84, proximal to the distal end cap, i.e. in embodiments in which all the supply fluid 41 being pumped would be redirected by the distal cap.

C. Adjunct Drug Therapy

Figure 19A:
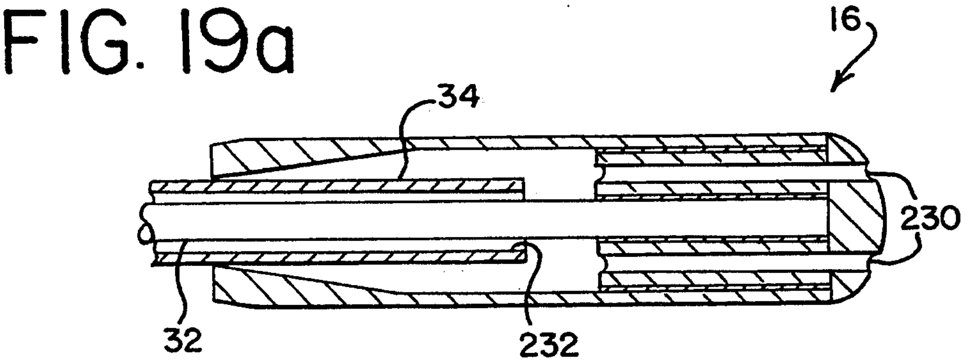
FIGS. 19*a* to 19*c* depict alternative embodiments of the distal tip adapted for drug delivery.
Figure 19B:
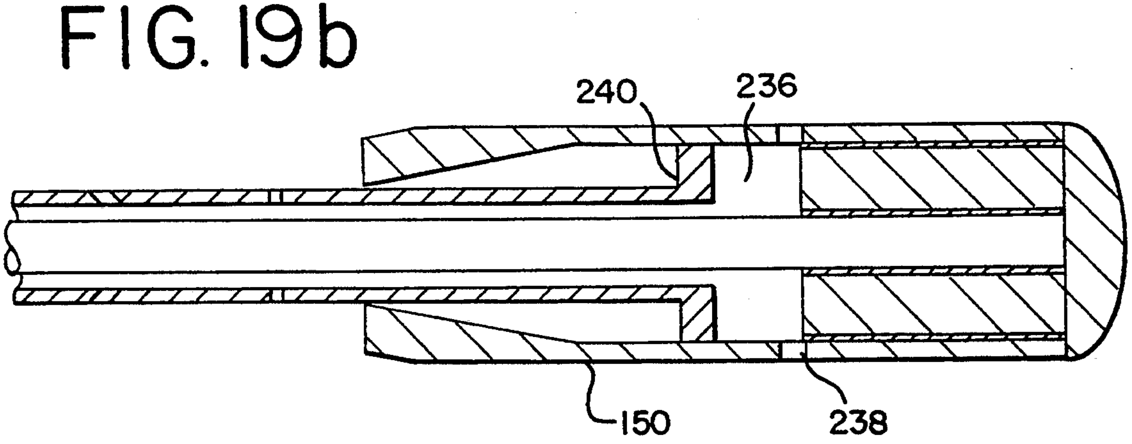
Figure 19C:
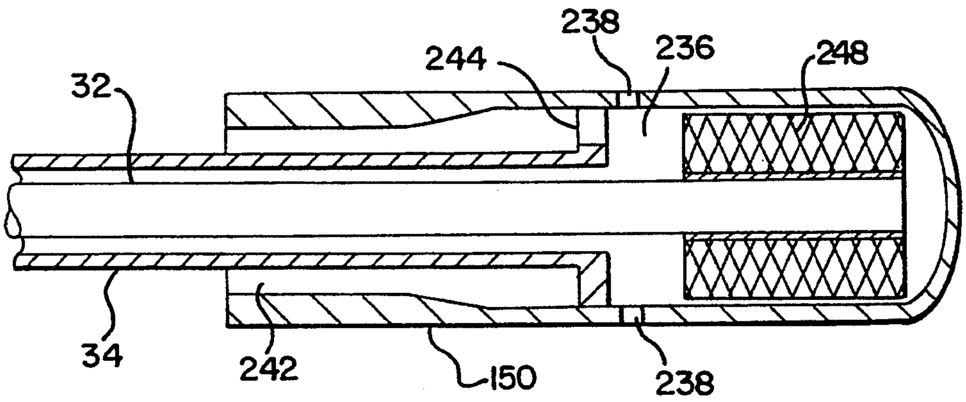

Referring again to FIG. 3, in an alternative embodiment, the annular region 92 between the wire support tube 34 and the damping sheath 36 can be used as a path for introducing various drug or biological fluid therapies intravascularly to promote thrombus or fibrous material dissolution and dispersal. In further alternative embodiments, drug therapies may be applied to a stenosis site via the distal tip 16 of the catheter assembly 14. FIGS. 19*a*, 19*b*, and 19*c* depict alternative distal tip embodiments adapted for drug delivery. FIG. 19*a* is an alternative embodiment of the distal tip having drug delivery ports 230 extending therethrough to provide an immediate path to the lesion site. This path provided by ports 230 would be available during the procedure and lesion crossing. In this embodiment, the drug therapy would be delivered via the annular region 232 between the core wire 32 and the supply tube 34.

FIGS. 19*b* and 19*c* depict alternative embodiments in which the relatively high frequency oscillations generated at the tip 16 are harnessed to inject drug therapies into the lesion site. A pumping action could be generated by the moving core wire 32 or distal tip 16. In both the embodiments depicted in FIGS. 19*b* and 19*c*, a pumping chamber 236 is formed in the distal tip 16. The pumping chamber 236 communicates with injection ports 238 oriented laterally from the end cap 150. Therapeutic drugs could be introduced into the pumping chamber 236 by way of the annular region between the core wire 32 and the supply tube 34 or by another lumen provided especially for this purpose, e.g. as shown in FIG. 19*c*. Referring to FIG. 19*b*, a proximal chamber seal 240 is located on and connected to the distal end of the supply tube 34 inside the tip 16. The chamber seal 240 forms the proximal side of the chamber 236. Drug therapies supplied to the chamber 236 are injected in the vessel environment through the ports 238 by the pumping action of the tip relative to the core wire 32. In FIG. 19*c*, the drug therapy is provided via a separately provided lumen 242 and delivered to the pumping chamber 236 via a port 244. The distal end of the core wire 32 is connected to a piston 248 which moves independently of the cap 150.

D. Distal Sheath Guide Embodiment

Figure 20:
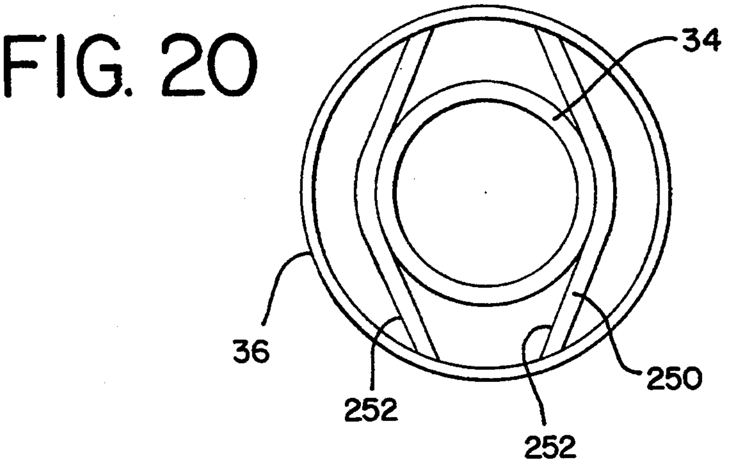
FIG. 20 is a cross sectional view of an intermediate portion of the catheter assembly illustrating an alternative embodiment of the distal particle removal sheath support guide.

In the embodiment described above and depicted in FIG. 3, the distal sheath guides 112 are formed of a plurality of radially extending leaf springs. In a further alternative embodiment depicted in FIG. 20, the distal sheath guide may be composed of a thin wall hypotube 250 formed into struts 252 from the support tube 34 to the particle removal sheath 36.

E. Proximal Spring-Mass Embodiments

Figure 21:
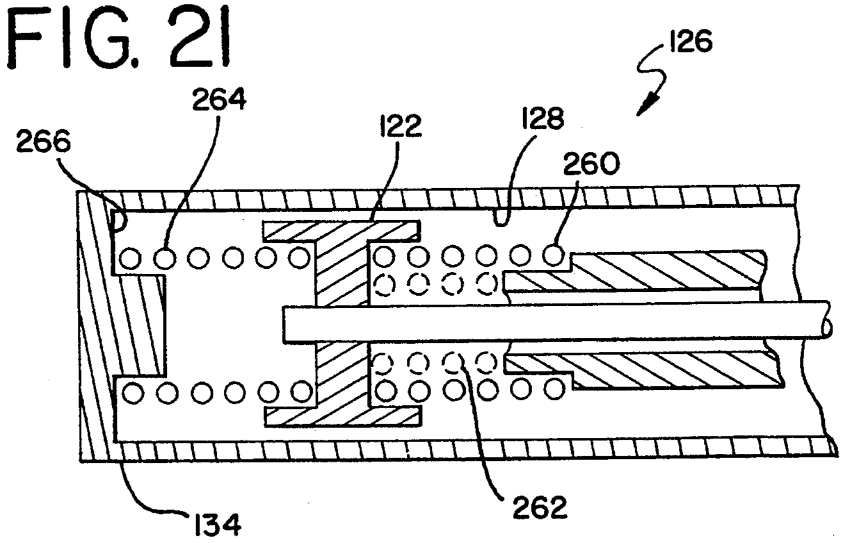
FIG. 21 is a cross sectional view of the proximal portion of the catheter assembly depicting an alternative embodiment of the mass-spring system.

In the embodiment described above and depicted in FIG. 6, the mass 122 is connected to the spring 130 to form a mass-spring system 132 specifically constructed to cooperate with the driving apparatus to impart oscillation to the core wire. In a further alternative embodiment, the mass-spring system may be composed of a mass associated with multiple springs. An alternative embodiment incorporating multiple springs in a mass-spring system is shown in FIG. 21. The multiple springs can be attached to the moving mass in either series or parallel fashion. In the embodiment shown in FIG. 21, three springs are utilized. A first spring 260 is connected to the proximal mass 122 and the spring bushing 60 in a location corresponding the that of the spring 130 of the embodiment described above. In addition, a nested spring 262 is located interior of and coaxial to the first spring 260. This spring may have a different spring constant and/or stiffness. A third spring 264 is located proximal of the mass 122 between the mass and a proximal wall 266 of chamber 128. All springs may have different spring constants and/or stiffnesses. These springs may be fabricated from various materials ranging from high strength stainless steels possessing high endurance limits to highly efficient polymers such as dense rubbers with storage efficiencies on the order of 90 percent or combinations thereof. These modifications to the spring and its mounting would affect the operating frequency of the system due to their impact on system stiffness.

Attachment of the springs 130, 260, 262, and 264 to the mass 122 and/or spring mounting bushing 60 can be accomplished by any biologically compatible method, including bonding, soldering, brazing, or welding. The present embodiment uses soldering.

In a further embodiment, the proximal mass 122 can be varied in size depending on the desired force performance required. The force available through the mass is directly proportional to the mass diameter. Mass diameter can be increased while reliefs in the mass can be provided to maintain the inherent mass size.

F. Embodiment with Dilation Balloon

Figure 22:
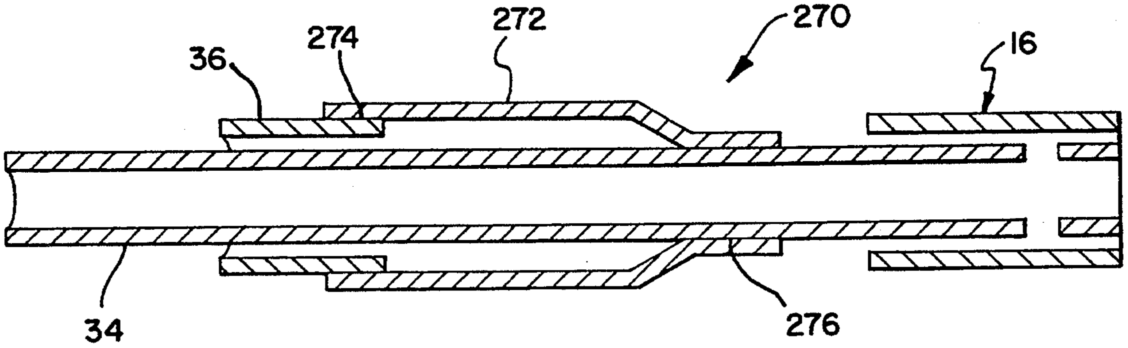
FIG. 22 is a cross sectional view of a distal portion of an alternative embodiment of the catheter assembly incorporating an inflatable dilation balloon.

Referring to FIG. 22, there is depicted a further embodiment 270 of the present invention in which a dilation balloon is incorporated onto the catheter assembly 14. As mentioned above, one way in which the system 10 may be used is to recanalize an obstructed vessel site so that a conventional dilation balloon can be installed across the site in order to perform an angioplasty procedure. In the embodiment 270 of FIG. 22, a conventional dilation balloon 272 is incorporated onto the catheter assembly 14. Thus, instead of withdrawing the catheter assembly 14 after an obstruction has been recanalized in order to install a dilation balloon catheter, the dilation balloon is already on the catheter assembly so that the physician can proceed with the dilation as soon as the obstruction is crossed by the tip 16. This can reduce the time involved in treating an obstruction and also eliminate the need for crossing the obstruction again with a separate balloon catheter through the recanalized vessel. In the embodiment shown in FIG. 22, the balloon 272 is bonded proximally at 274 to the second tube 36 and bonded distally at 276 to the first tube 34. In this embodiment, the annular region between the first tube 34 and the second tube 36 is used for conveyance of inflation fluid for the balloon 272.

G. Outer Sheath with expanding tip

Figure 23:
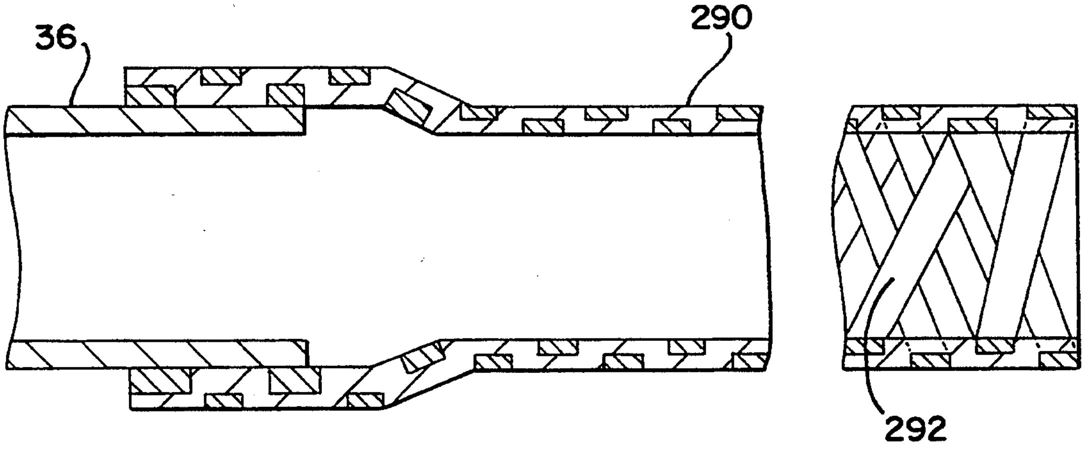
FIG. 23 is a cross sectional view of an distal portion of an alternative embodiment of the second tube portion of the catheter assembly incorporating an expanding tip to facilitate exchange of intravascular devices.

Referring to FIG. 23, there is depicted another embodiment of the present invention. In the embodiment of FIG. 23, the damping sheath 36 is provided with an expanding tip 290. In this embodiment, the damping sheath 36 is used with a supply tube and core wire (neither shown in FIGS. 23*a* and 23*b*) in a catheter assembly as in the embodiments described above. The expanding tip 290 may be provided by means of incorporating a braid 292 into the material of the damping sheath construction. This embodiment of the present invention provides for facilitating exchange of intravascular devices for the treatment of a vessel obstruction. The expanding tip 290 of the embodiment represented in FIG. 23*a* and 23*b* provides for expanding the diameter of the distal portion of the second tube 36 from a first (or smaller) diameter to a second (or larger) diameter. The first diameter is the diameter at which the second tube 36 is used for the recanalization of an obstructed artery by the application of low frequency mechanical energy or cavitation, in a manner according to the embodiments described above. At the second diameter, the distal portion of the second tube is large enough so that the supply tube and distal tip may be withdrawn proximally from the second tube 36. Then, the second tube may be used as an introducer sheath to allow the positioning of another intravascular device to the vessel site. The other intravascular device may be a balloon catheter, an atherectomy device, or even another supply tube with a distal tip.

In an exemplary method of use, the catheter assembly 14 incorporating the second tube with the expanding tip 290 in the first or smaller diameter is advanced to the vessel site obstruction as in the previously described embodiments. The distal tip is oscillated to impart low frequency mechanical energy to the vessel obstruction or to cause cavitation at the vessel site obstruction. The distal tip is advanced through the obstruction thereby recanalizing that portion of the vessel. After the distal tip and the portion of the second tube including the expanding member 290 is past the obstruction, the expanding member 290 is expanded from the first to the second diameter so that the first tube and distal tip can be withdrawn from the second tube. Then, a balloon dilation catheter is advanced through the lumen of the second tube to the site of the recanalization. The second tube is withdrawn proximally leaving the balloon portion of the dilation catheter exposed to the recanalization site. Then, the balloon can be inflated to further treat the vessel obstruction as in a conventional angioplasty. An advantage of the above described procedure is that after recanalization, a balloon catheter can be advanced across a vessel obstruction by means of the access provided by the second tube thereby facilitating provision of therapy to the site.

I. Core Wire Alternative Embodiments

There are several core wire alternative embodiments that may provide potentially improved constrained axial stiffness and flexibility.

Figure 24A:
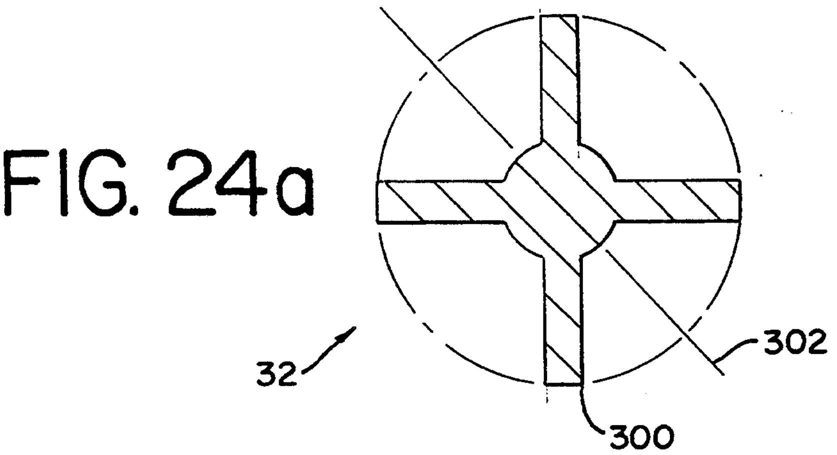
FIGS. 24*a* and 24*b* are cross sectional views depicting alternative embodiments of the core wire.

A first alternative core wire construction is shown in FIG. 24*a*. In the first alternative core wire construction, the core wire 32 could possess a profile in the form of a spline 300 such that the bending stiffness would be less in a given plane, e.g. plane 302. The constrained axial stiffness would not be compromised due to the addition of splines along the core wire shaft. The number of splines could vary depending on the required stiffness for a given application. Four splines may be suitable although fewer or more may be desired. Also the use of splines would reduce overall system mass allowing an increase in frequency of operation for the system. In further alternative embodiments, the core wire cross section could possess a profile other than round or splined. For example, the core wire profile could be triangular, square, rectangle, or other geometrically beneficial cross sections. These alternative core wire embodiments may possess desirable features similar to the spline profile embodiment.

Figure 24B:
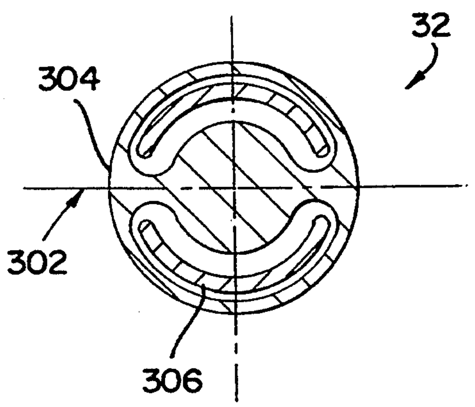

A second alternative core wire construction is shown in FIG. 24*b*. In this alternative embodiment, the core wire 32 would have a composite construction with a multiple lumen polymer extrusion 304 into which prestressed (radially) members 306 are installed to yield a stiffening force on the polymer lumen. This embodiment would allow reduction in the overall system mass due to the hybrid or composite construction of the core wire and variability in core wire stiffness based on prestressing of the internal member. This embodiment would also provide for preferred bending planes, e.g. plane 302.

A third alternative core wire embodiment includes a composite shaft using filament members assembled in a resin or polymer. A fiber orientation can substantially increase a component's stiffness in one direction while having a lesser impact on stiffness in other directions or axes. This attribute would be utilized to increase the constrained axial stiffness of the core wire shaft while continuing to afford a lesser bending stiffness for flexibility.

A yet further alternative embodiment of the core wire 32 would be to form the core wire of a wire rope construction with a low coefficient of friction jacket. The shear plane inherent to a rope construction would allow this alternative core wire embodiment to have good bending flexibility while maintaining a high constrained axial stiffness.

J. Operating Mode Alternatives

Retrieval of the ablated particulate could be accomplished by using a rotational retrieval means similar to an auger effect. Through viscous forces on the fluid and the rotation of the particulate transmission sheath 36 relative to the support tube 34, a viscous pump could be established to transport debris proximally. The internal profile of the particulate transmission sheath 36 could be modified to promote a viscous attachment and/or the profile of the support tube 34 could also be modified to improve viscous attachment effect during relative rotation. In this alternative embodiment, the ablation of the obstruction would be accomplished through a combined effect of a distal orifice and the mechanical movement of the distal tip. Particulate transmission would be accomplished through the viscous pump and a proximal vacuum.

It is intended that the foregoing detailed description be regarded as illustrative rather than limiting and that it is understood that the following claims including all equivalents are intended to define the scope of the invention.

We claim:

1. An apparatus for recanalization of an obstruction in a blood vessel characterized by the presence of undesired material at a site in the blood vessel comprising:

a wire support tube adapted to be positioned intravascularly in the patient, said wire support tube having a proximal portion locatable outside the patient's vessel and a distal portion adapted to be positioned in the patient's blood vessel at the site of the obstruction;

a wire located within and extending through said wire support tube, said wire adapted to move axially with respect to said wire support tube;

a tip connected to a distal end of said wire and extending distally from the distal portion of the wire support tube;

a driving apparatus positioned at said proximal portion of the wire support tube and adapted to impart energy to said wire located therein to move said wire in oscillation axially with respect to said support tube;

a second tube located around at least a distal portion of the wire support tube, said second tube adapted to damp transverse movement of the wire support tube or wire caused by wire oscillations;

a pressurized fluid supply connected to said proximal portion of said wire support tube and adapted to convey pressurized fluid distally in said support tube along said wire to a distal opening of said wire support tube directed at a channel in said tip adapted to redirect the pressurized fluid from said wire support tube distal opening toward a distal opening of said second tube formed by the annular region between said wire support tube and said second tube; and an exhaust port connected to a proximal portion of said second tube and adapted to withdraw effluent from the second tube conveyed from the distal opening thereof.

* * * * *